United States Patent [19]
Kellenberger

[11] Patent Number: 5,147,343
[45] Date of Patent: Sep. 15, 1992

[54] ABSORBENT PRODUCTS CONTAINING HYDROGELS WITH ABILITY TO SWELL AGAINST PRESSURE

[75] Inventor: Stanley R. Kellenberger, Appleton, Wis.

[73] Assignee: Kimberly-Clark Corporation, Neenah, Wis.

[21] Appl. No.: 334,260

[22] Filed: Apr. 10, 1989

Related U.S. Application Data

[63] Continuation-in-part of Ser. No. 184,302, Apr. 21, 1988, abandoned.

[51] Int. Cl.$^5$ .................. A61F 13/15; A61F 13/20
[52] U.S. Cl. ..................... 604/368; 604/372; 604/375; 428/281; 428/283
[58] Field of Search ............ 428/281, 283; 604/368, 604/372, 375

[56] References Cited

U.S. PATENT DOCUMENTS

| | | | |
|---|---|---|---|
| Re. 32,649 | 4/1988 | Brandt et al. | 604/368 |
| 3,670,731 | 6/1972 | Harmon | 604/368 |
| 3,954,721 | 5/1976 | Gross | 604/368 |
| 4,069,177 | 1/1978 | Smith | 260/17.4 GC |
| 4,090,013 | 5/1978 | Ganslaw et al. | 526/15 |
| 4,102,340 | 7/1978 | Mesek | 128/287 |
| 4,104,214 | 8/1978 | Meierhoefer | 260/17.4 CL |
| 4,105,033 | 8/1978 | Chatterjee et al. | 128/285 |
| 4,155,893 | 5/1979 | Fujimoto et al. | 260/29.6 H |
| 4,242,408 | 12/1980 | Evani et al. | 428/290 |
| 4,381,782 | 5/1983 | Mazurak et al. | 604/368 |
| 4,389,487 | 6/1983 | Ries | 435/273 |
| 4,535,098 | 8/1985 | Evani et al. | 521/149 |
| 4,666,975 | 5/1987 | Yamasaki et al. | 524/733 |
| 4,699,823 | 10/1987 | Kellenberger et al. | 604/378 |
| 4,742,086 | 5/1988 | Masamizu | 521/62 |
| 4,773,903 | 9/1988 | Weisman et al. | 604/368 |
| 4,798,603 | 1/1989 | Meyer et al. | 604/378 |

FOREIGN PATENT DOCUMENTS

| | | |
|---|---|---|
| 0198683 | 10/1986 | European Pat. Off. |
| 0202125 | 11/1986 | European Pat. Off. |
| 0202127 | 11/1986 | European Pat. Off. |
| 0258120 | 3/1988 | European Pat. Off. |
| 0304319 | 2/1989 | European Pat. Off. |
| 2222780 | 11/1973 | Fed. Rep. of Germany |
| 2293914 | 12/1975 | France |
| 63-99861 | 5/1988 | Japan |

OTHER PUBLICATIONS

"Determination of the Fluid Capacity of Some Commercial Catamenial Tampons", by M. Louis Arin, Ph.D.

"The Concept of Superabsorbent Polymer", by Dr. F. Masuda of Sanyo Chemical Industries Ltd. presented as Paper No. 13 at the Pira Fibramerics Program held Dec. 1-3, 1987.

Arakawa Technical Data by Arakawa Chemical (USA) Inc., 625 N. Michigan Ave., Suite 1700, Chicago, Ill. 60611-"Absorbency of Absorbent Polymer Under Pressure".

Aquareserve Technical Note by Nippon Gohsei-"High Water Absorbing Synthetic Resin" Technical Note 3.

Primary Examiner—Randall L. Green
Assistant Examiner—Paul Prebilic
Attorney, Agent, or Firm—Thomas J. Mielke

[57] ABSTRACT

An absorbent composite of the type comprising a porous matrix of fibers and a superabsorbent material dispersed among the interfiber spaces (pores) wherein the superabsorbent material exhibits the ability to absorb greater than about 24 milliliters of a saline solution per gram of superabsorbent material under an applied restraining force of at least about 21,000 dynes/square centimeter provided that, when in the form of discrete particles, at least about 50% of said superabsorbent material has a size greater than the median pore size of the matrix when wet.

40 Claims, 16 Drawing Sheets

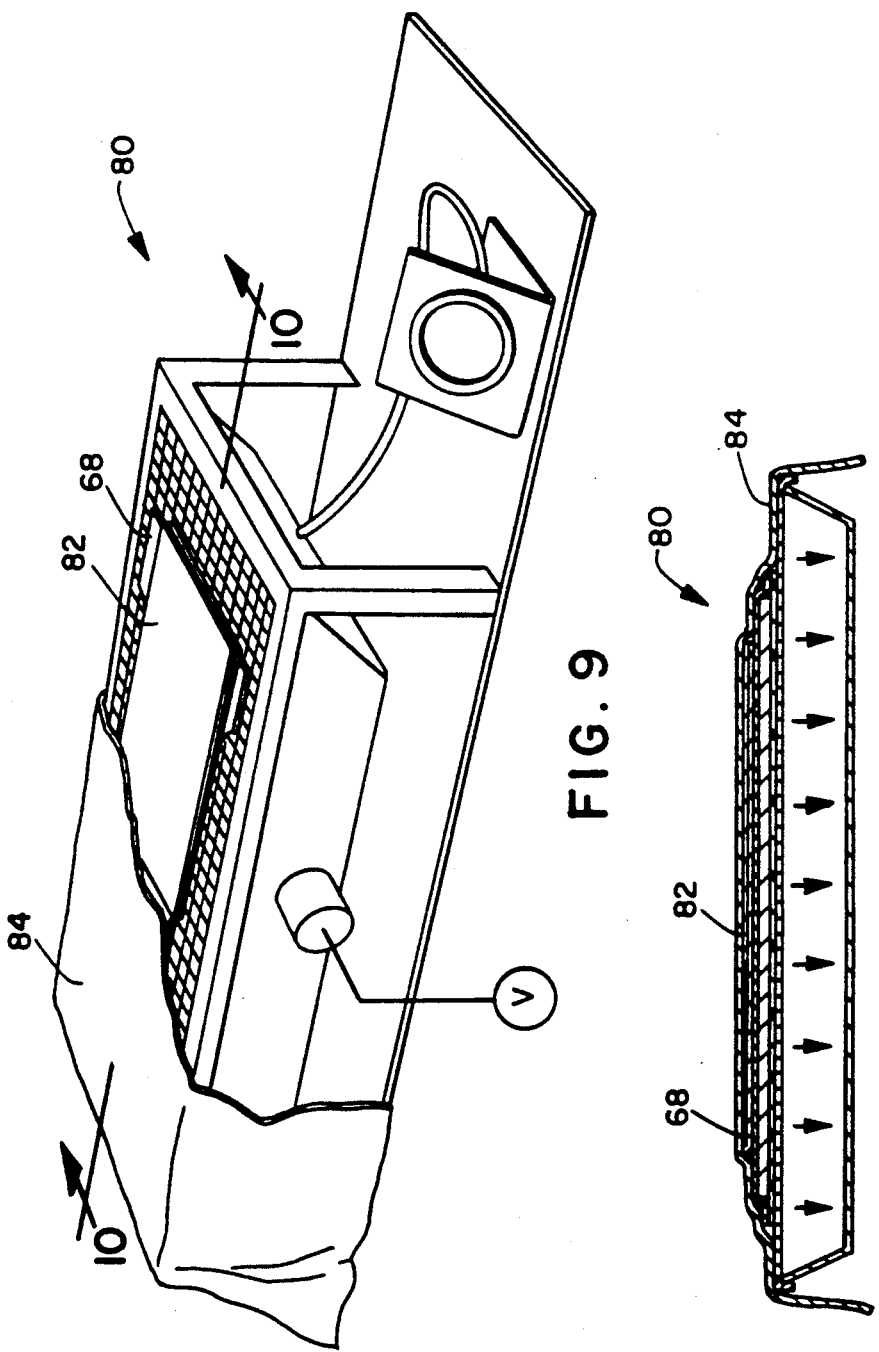

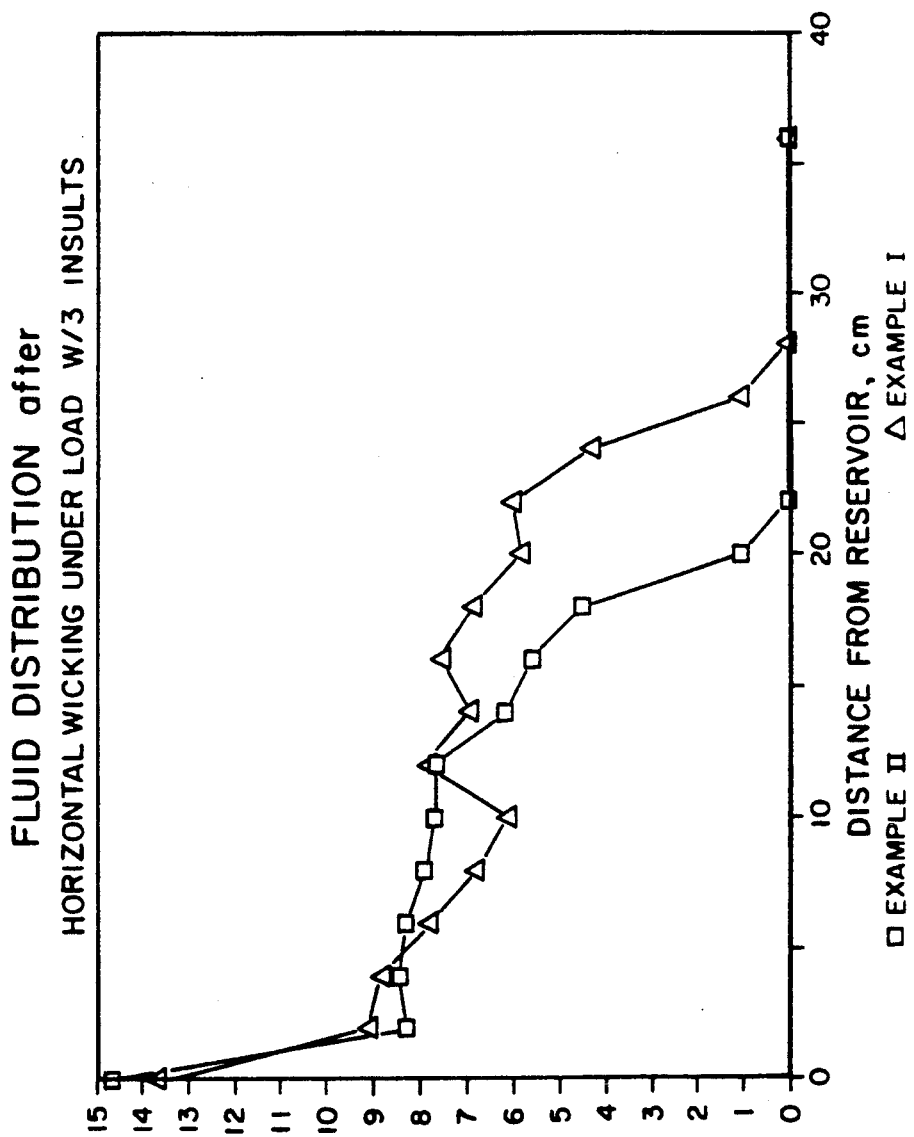

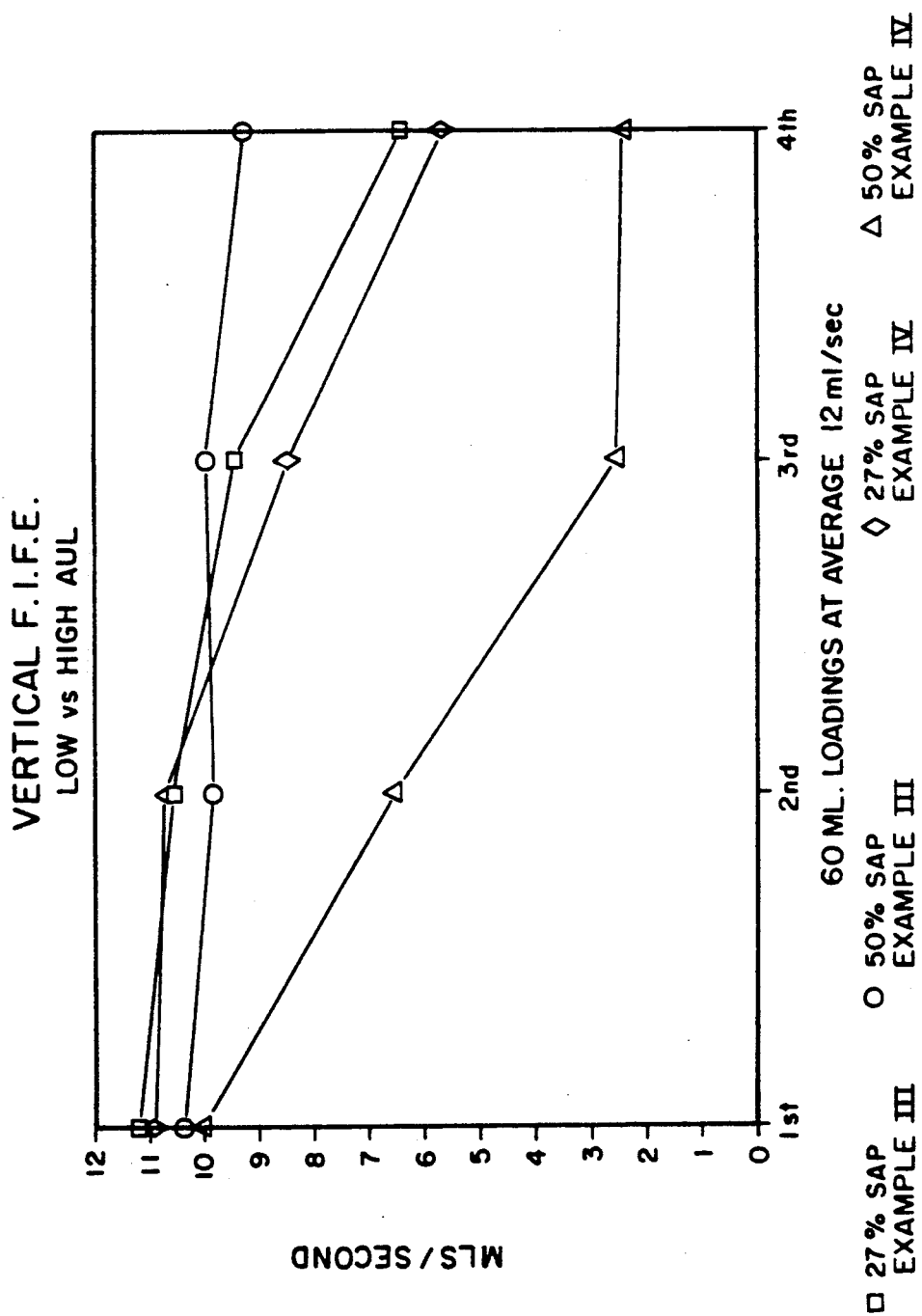

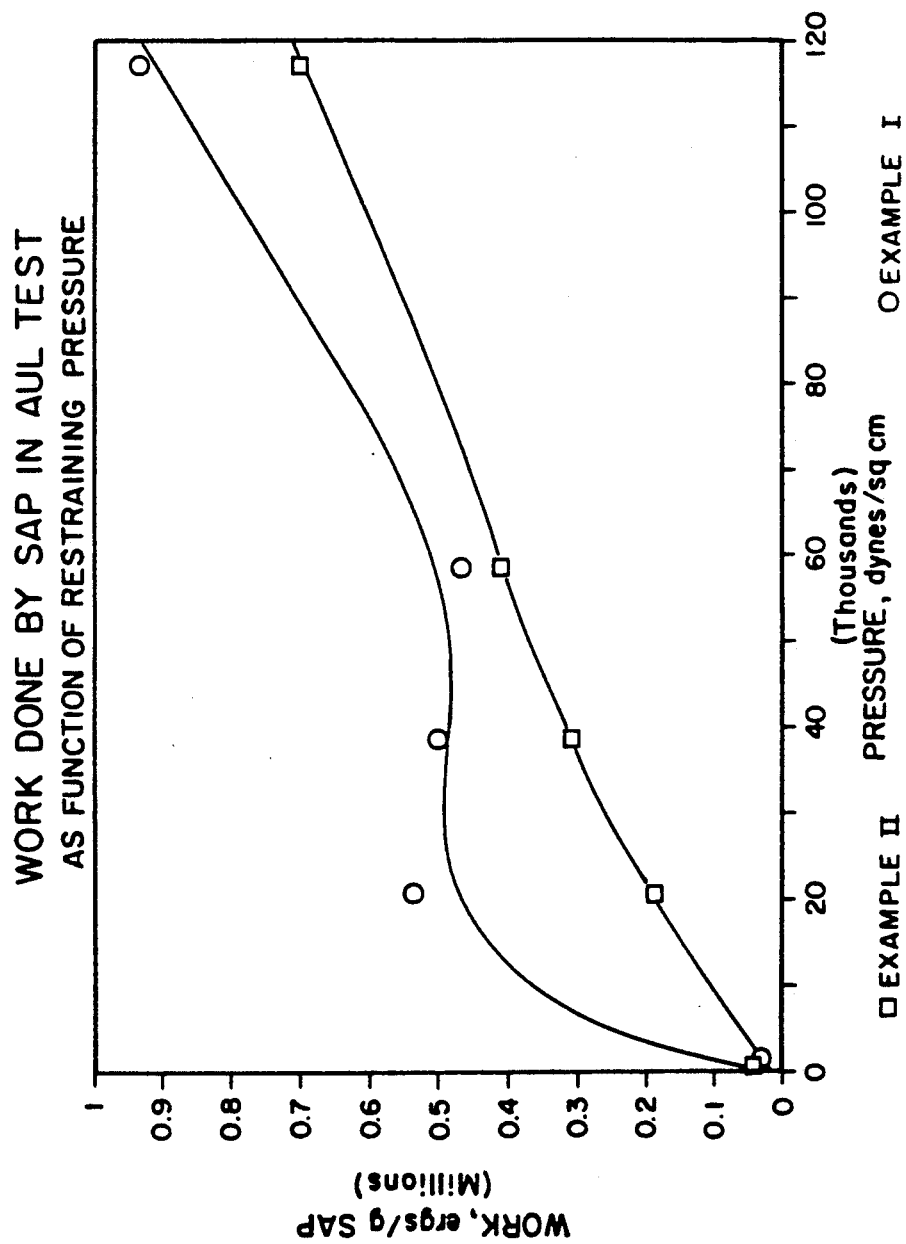

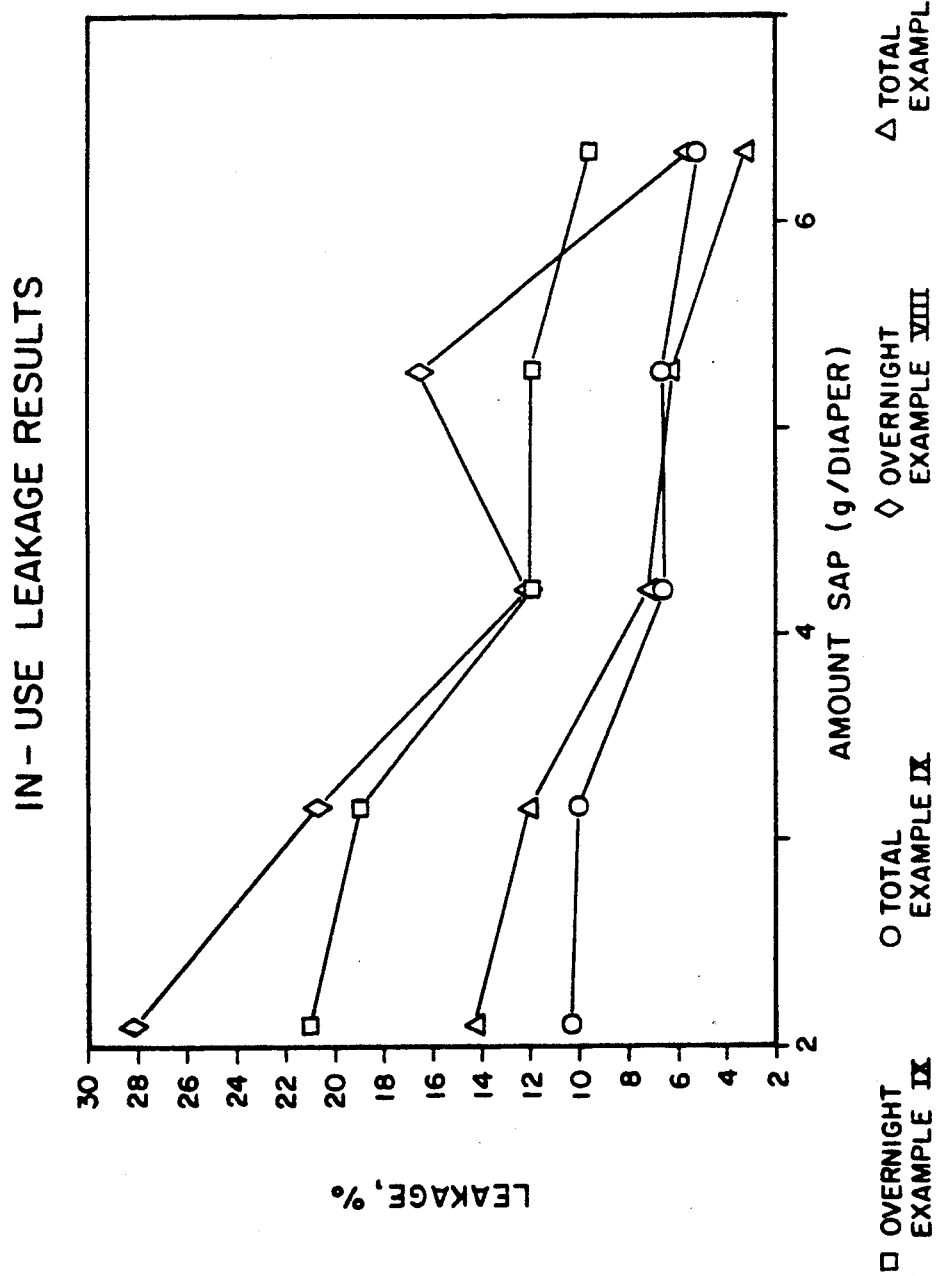

ABSORBENT PRODUCTS CONTAINING HYDROGELS WITH ABILITY TO SWELL AGAINST PRESSURE

This application is a continuation-in-part of U.S. Pat. No. 07/184,302 filed Apr. 21, 1988 now abandoned.

FIELD OF THE INVENTION

This invention relates to improved absorbent composites containing hydrogel-forming polymers (superabsorbents) such as ionic hydrocolloids which, upon contacting fluids, such as body liquids (urine), imbibe such liquids and thereby form hydrogels. Such absorbent structures can be incorporated into absorbent articles such as disposable diapers, adult incontinence pads, sanitary napkins and the like.

BACKGROUND OF THE INVENTION

Superabsorbent polymer (hereinafter referred to as SAP) and superabsorbent material are not technical terms. A more precise designation for present hydrogel-forming SAP is ionic hydrocolloid. There is general understanding in industry that to be called superabsorbent, a material should imbibe, absorb or gel about 10 times its own weight of fluid and retain it under moderate pressure. The fluid is taken into the molecular structure and not simply contained in pores from which it could be expressed by squeezing. The hydrogels used in soft contact lenses, semi-permeable membranes and ion-exchange resins are not superabsorbent. Inorganic materials and polysaccharides, which can gel fluids upon manipulation of solutions, are not superabsorbents unless they can generate a gel when simply exposed to the fluid.

It is commonly thought that SAP was invented about 1970 by USDA researchers studying grafted starch, as described in *Absorbency* by P. K. Chatterjee, editor, pages 197-198, Elsevier, New York, N.Y., (1985). Absorbent or gelling polymers are actually much older. As early as 1952, carboxylic ion-exchange resins were known which swelled up to 500-fold in sodium bicarbonate, as described in British patent 719,330 to Bayer. Nevertheless, the application of these absorbent polymers in consumer products was not to be recognized until much later. In 1954, a technique was disclosed for making swellable polymers in saturated magnesium sulfate solution in U.S. Pat. No. 2,810,716 to Markus wherein it was suggested that such polymers could be used in drug delivery. U.S. Pat. No. 3,229,769 to Bashaw and Harper issued Jan. 18, 1966 disclosed a lightly crosslinked poly(potassium acrylate) for gelling water used in fire-fighting. In 1966, such gelling polymers were actively being promoted for use in disposable sanitary products and soon thereafter, U.S. Pat. No. 3,669,103 to Harper et al. disclosed various medical and personal care uses of acrylic acid and acrylamide-based gelling polymers. This is probably one of the first suggestions in the literature for the use of synthetic polymers in gelling (absorbing) aqueous body fluids.

Since this time period, many synthetic SAPs have been made which are directly descended from these early materials.

Present commercially available SAPs are typically crosslinked poly(acrylic acid) or acrylic acid grafted on starch. The carboxyl functionality is partially neutralized with sodium or potassium hydroxide. Some versions made for agricultural purposes, particularly in Japan, involve graft polymerizing acrylonitrile onto gelatinized starch followed by hydrolysis of the polyacrylonitrile to poly(acrylic acid-co-acrylamide). Although primarily acrylic acid-based SAPs are disclosed in conjunction with the present invention, it should be understood that other types of SAP may be contemplated for use.

In the solution polymerization of partially neutralized acrylic acid, aqueous sodium hydroxide is mixed with a water solution of acrylic acid. The crosslinker (a difunctional monomer) is added followed by the free radical polymerization initiator. This method yields a rubbery continuous gel which is dried and ground to the desired particle size.

The suspension or inverse emulsion technique involves dispersing aqueous monomer and crosslinker in a hydrocarbon diluent. Organic-soluble free radical initiators are usually employed. Suspension polymerization gives spherical particles with the size controlled by the type and amount of suspending agent. The water is azeotropically removed and the particles recovered by filtration.

Although the actual operating conditions used by current producers of SAP may vary, the patent literature teaches a broad range of temperature, concentrations, types of initiators and crosslinkers. Patents which disclose hydrogel-forming polymer compositions for use in absorbent structures are listed below:

U.S. Pat. No. 3,901,236 to Assarsson et al.
U.S. Pat. No. 4,062,817 to Westerman
U.S. Pat. No. 4,076,663 to Masuda et al.
U S. Pat. No. 4,286,082 to Tsubakimoto et al.
U.S. Pat. No. 4,340,706 to Obayashi et al.
U.S. Pat. No. 4,473,689 to Login et al.
U.S. Pat. No. 4,535,098 to Evani et al.
European Patent 75,510
German Patent 3,313,344

The prior art has recognized the independent operating variables of gel stiffness and retention capacity, particularly, U.S. Pat. Re. 32,649 to Brandt et al., which stresses high retention capacity of the gel, once swollen, upon a subsequently applied load.

However, the prior art has not heretofore recognized the importance of providing absorbent structures having hydrogel-forming polymers capable of swelling against an applied restraining force. Instead, the prior art, particularly the aforementioned U.S. Pat. Re. 32,649, only discloses the ability of a gel particle to retain fluid under an applied pressure after the gel has been allowed to freely swell, that is, without a restraining force applied during swelling.

SUMMARY OF THE INVENTION AND ADVANTAGES

It is an object of the present invention to provide an absorbent composite for a disposable sanitary article which will not only retain fluid under an applied restraining force, but will also absorb fluid under actual pressures exerted by the body during use.

This and other related goals are achieved in an absorbent composite comprising a porous matrix of fibers and superabsorbent material wherein the superabsorbent material, can absorb at least about 24 milliliters of an aqueous solution of sodium chloride containing 0.9 percent, by weight, sodium chloride, per gram of superabsorbent while under a restraining pressure of at least 21,000 dynes per square centimeter provided that, when in the form of discrete particles, at least about 50%, by weight, of the superabsorbent material has a size greater than the median pore size of said porous matrix, when wet.

In a preferred form of the invention, there is provided a disposable sanitary article, most preferably a diaper or incontinence garment, comprising a liquid-impermeable backsheet, a liquid-permeable topsheet coterminous with the backsheet and the absorbent composite structure of the present invention sandwiched therebetween.

In a preferred form, the absorbent composite structure of the present invention has an average density in a range from about 0.10 to 0.15 gms./cubic cm.; moreover, the preferred hydrocolloid particles of the invention comprise a polyacrylate-based composition.

BRIEF DESCRIPTION OF THE DRAWINGS

FIG. 9 is a perspective view, showing a fluid flowback testing apparatus used to evaluate absorbent composite of the type described herein;

FIG. 10 is a cross-sectional view of FIG. 9;

FIGS. 14–22 are graphs summarizing data from tests on the absorbent composites of Examples I–IX, according to the test methods described herein.

The above Figures may be more fully understood with reference to the accompanying Detailed Description.

DETAILED DESCRIPTION OF THE PREFERRED EMBODIMENT

Figure 1:
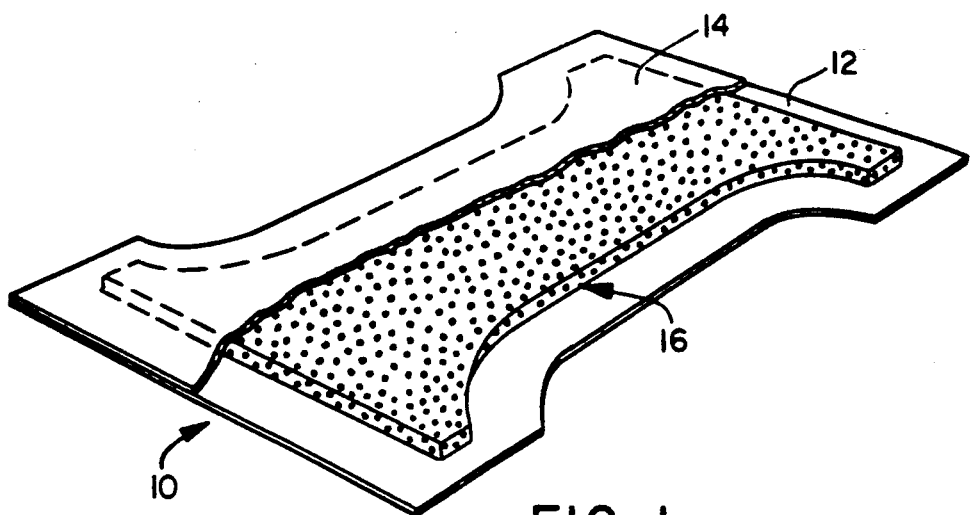
FIG. 1 is a cut-away view of a disposable diaper which is a preferred configuration for the absorbent articles contemplated herein.

According to FIG. 1, there is generally shown a disposable sanitary absorbent article 10, such as an infant diaper or adult incontinence garment, of the type having a liquid-impermeable backing material 12, a liquid-permeable facing material 14 and a liquid absorbent composite, generally indicated at 16, sandwiched therebetween. In its preferred form, the absorbent article 10 defines a generally hourglass shape having a pair of waist sections situated at opposed longitudinal ends of the article 10, a pair of opposed lateral sides extending between and interconnecting the ends and leg cut-outs along the sides. The leg cut-outs may be further provided with elasticized gathers (not shown) for the purpose of conforming the intermediate crotch section of the diaper to the body of a wearer and also aiding in the prevention of lateral spillage of wastes outwardly from the sides onto outer clothing of a wearer. The article may be provided with adhesive tape fasteners (not shown) of the type known in the art to secure it about the body. The liquid-impermeable backing material 12 may be made from a commercially available polyolefin film and the liquid-permeable bodyside facing material 14 may be made from a commercially available nonwoven material, such as a spunbonded or carded fibrous web which is wettable and capable of passing urine.

Figure 2:
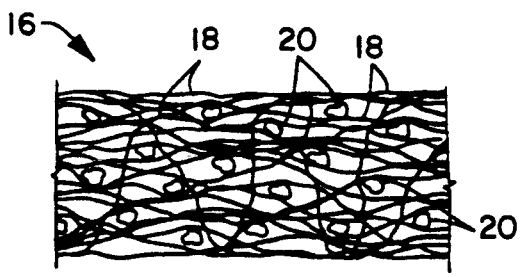
FIG. 2 is an enlarged cross-sectional view of FIG. 1, showing the dry absorbent composite of the present invention.
Figure 4:
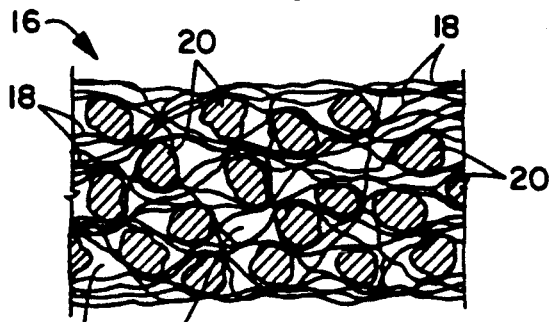
FIG. 4 is an enlarged cross-sectional view of FIG. 1, showing the absorbent composite of the present invention, when wet.

The absorbent composite 16 of the present invention preferably comprises a porous matrix of fibers 18, as shown in greater detail in FIGS. 2 and 4, and superabsorbent material 20 dispersed among the interfiber spaces or pores 22. The superabsorbent material need not be discrete particles as illustrated, but could take the form of continuous or discontinuous fibers. Therefore, the description herein of suitable super absorbent material should not be taken so as to limit the claims to exclude non-particulate SAP. The porous fibrous matrix of the composite 16 is preferably an air-laid batt of fluff, which may be formed in a variety of ways, for example, according to the teachings of Mazurak and Fries, as set forth in U.S. Pat. No. 4,381,782, the entire disclosure of which is incorporated herein by reference and relied upon.

Although comminuted wood pulp (fluff) is preferred to form the matrix for this invention, other wettable fibers such as cotton linters can be used. Additionally, the porous matrix may be formed from meltblown synthetic fibers such as polyethylene, polypropylene, polyesters, copolymers of polyesters and polyamides, and the like. The matrix may also be formed from a mixture of wood pulp fluff and the meltblown fibers discussed above. For example, the matrix may comprise at least about 5 weight percent preferably about 10 weight percent synthetic polymer fibers and the remainder may comprise wood pulp fluff. The fibers of the matrix are generally hydrophilic or rendered hydrophilic through a surface treatment.

The preferred wood pulp fluff is northern or southern softwood kraft wood pulp (that is, made according to the sulfate process commonly known in the art) which has been bleached. Exemplary is a bleached southern pine kraft wood pulp that can be purchased from ITT Rayonier or International Paper Company. A hardwood kraft wood pulp may also be used. A suitable hardwood pulp is southern hardwood kraft obtainable from Weyerhaeuser as "New Bern 309." The hardwood or softwood fluffs may be used separately or in blends, as taught by U.S. Pat. No. 4,699,619 to Bernardin, the entire disclosure of which is herein incorporated by reference and relied upon. For example, when a blend is used the weight ratio of softwood kraft pulp to hardwood kraft pulp can be from 1:3 to 20:1.

The term "density" as used herein refers to the density of the composite absorbent structure 16 and not just the fiber density. The density of the composite 16 should be in the range of about 0.03 to about 0.40 gms./cubic cm., beneficially from about 0.08 to about 0.3 gms/cubic cm, most beneficially from about 0.1 to about 0.2 gms/cubic cm, with the preferred range, in light of considerations of integrity and bulk, from about 0.10 to about 0.15 gms./cubic cm. The density, for the purpose of this application, is measured under a load of 0.2 psi.

The composite 16 may be densified to a desired density in either a heated or unheated press, such as can be obtained from Dake, Grand Haven, Mich., as a "Dake Laboratory Press," Model No. 44-148, which includes a (heated) platen operated under suitable conditions of temperature and pressure as known in the art to achieve the desired density. Alternatively, a calendar nip which may be heated, is suitable for use in the densification process, as known in the art.

As used herein the term "superabsorbent" refers to a material, natural or synthetic, capable of absorbing or gelling at least about 10 times its weight in liquid. In one embodiment of the present invention the superabsorbent material comprises a hydrocolloid, preferably an ionic hydrocolloid. Exemplary of superabsorbent material suitable for use in the present invention are polyacrylamides; polyvinyl alcohol; ethylene maleic anhydride copolymers; polyvinyl ethers; hydroxypropylcellulose; carboxy-methycellulose; polymers and copolymers of vinyl sulfonic acid; polyacrylates; starch grafted polyacrylates; and the like.

The superabsorbent materials of the present invention are generally dispersed in the porous fiber matrix. As can be seen from reference to FIG. 2, when the superabsorbent material is in the form of discrete particles the particles are generally located within the pores of the fiber matrix.

The composite structures of the present invention generally comprise from about 5 to about 90 weight percent superabsorbent material, beneficially from about 10 to about 70 weight percent and preferably from about 10 to about 60 weight percent based on total composite weight.

Generally, superabsorbent material dispersed in a fibrous matrix enhances the fluid holding capacity of the composite. However, due to the swelling nature of the superabsorbent material, wicking in a horizontal plane of the fiber matrix may be severely hindered if the superabsorbent is not carefully selected. This aspect of the invention will be discussed in greater detail below in connection with FIGS. 2, 3 and 4.

Although prior art superabsorbent materials and absorbent composites made therewith have favorably exhibited the ability to freely swell with fluid and retain such fluid against an applied pressure, the benefits of this characteristic are, to an extent, illusory. The reason for this is that to exhibit an improved performance in use, the superabsorbent material must also have the ability to initially imbibe fluid and swell while being subjected to a load. In use, such a load may be applied to the superabsorbent by the body of a person who is sitting or lying on the composite and/or by dynamic torsional pressures, e.g. during leg movement, while wearing a garment containing the absorbent composite.

The inventor has found that an absorbent composite 16 comprising a porous matrix of fibers 18 and superabsorbent particles 20 interspersed among the fibers 18 (FIGS. 1, 2 and 4) exhibits an improved performance when the particles 20 can swell against an applied restraining force of from about 10,000 to about 50,000 dynes/sq. cm. while performing an amount of work greater than about 300,000 ergs/gm of particles. Preferably, greater than about 500,000 ergs/gm of particles. These are the typical applied forces during use of, for example, a diaper as worn by a medium to large-sized infant.

For the purposes of this application the ability of a superabsorbent material to swell under an applied force and thereby perform work is quantified as the Absorbency Under Load or AUL. The AUL is expressed as the amount (in milliliters) of an aqueous sodium chloride solution (0.9 weight percent sodium chloride) which the superabsorbent material can absorb per gram in one hour under a load of 21,000 dynes per square centimeter. The amount of work performed by the superabsorbent is given by the formula:

$$W = (AUL) \times (\text{Restraining Force})$$

wherein W is work, AUL and restraining force (or load) are as defined above. For example, a superabsorbent having an AUL of 27 under a load of 21,000 dynes per square centimeter would perform an amount of work equal to $27 \times (21,000)$ or 567,000 ergs per gram of superabsorbent.

The method by which AUL is determined is set forth in greater detail below. The AUL is thought to be a function of the following factors; (1) gel stiffness while swelling, (2) ability to imbibe the fluid by osmotic and internal electrostatic repulsion forces, (3) surface wettability of the superabsorbent material, and (4) particle size distribution when wetted.

The inventor has discovered that it is desirable to employ superabsorbent materials having an AUL of at least about 24 and beneficially at least 27. The importance of employing a superabsorbent material having a relatively high AUL has been discussed briefly above. Specifically, it is often the case that the superabsorbent material will be located in a garment, such as a diaper, and the garment located, relative to the wearer, such that the superabsorbent material will be placed under a load or restraining force at the time it contacts the liquid to be absorbed. Accordingly, the superabsorbent material can only absorb the liquid if the superabsorbent is capable of performing work sufficient to overcome the restraining force. As a general rule, superabsorbent materials having an AUL of at least about 24 and beneficially at least 27 will be able to perform the amount of work necessary to overcome the restraining forces typically applied when the composites of the present invention are incorporated into the personal care products such as diapers, incontinence garments, sanitary napkins and the like. As a result of employing superabsorbent materials having an AUL of at least about 24, personal care products employing such superabsorbent materials have been found to perform better. Specifically, diapers employing such high AUL superabsorbent materials have been found to exhibit fewer overnight leaks.

In one preferred embodiment of the present invention, the porous fiber matrix is formed from cellulosic material such as wood pulp fluff. When the porous fiber matrix is formed from a cellulosic material the superabsorbent material has an AUL of at least 27.

In another preferred embodiment of the present invention, the porous fiber matrix comprises at least about 3 percent and preferably 5 percent, by weight, of a synthetic polymeric fiber and the remainder of the matrix is formed from cellulosic material. When the porous fiber matrix comprises synthetic polymeric fibers, the superabsorbent material has an AUL of at least about 24.

While employing a superabsorbent material with an AUL of at least 27 has been found generally capable of achieving the goals of the present invention, it is believed that employing superabsorbent materials with even higher AULs may be beneficial. Accordingly, the preferred superabsorbent materials will have an AUL of at least about 29 and the most preferred superabsorbent materials will have an AUL of at least about 32.

It has further been discovered that the ability to rapidly imbibe multiple fluid surges spaced in time from one another significantly improves the performance of the composite 16 when incorporated into a diaper.

Figure 3:
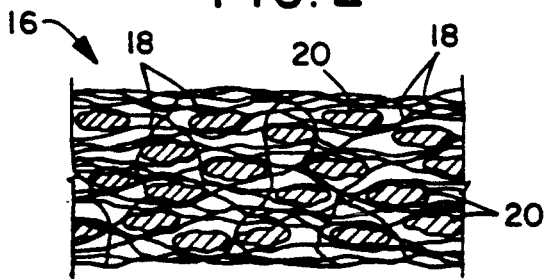
FIG. 3 is an enlarged cross-sectional view of an absorbent composite represented by the prior art when wet.

It is hypothesized that one important aspect in producing a composite with the ability to imbibe multiple fluid surges is the ability to maintain open capillaries in the porous fiber matrix after the first fluid application. Certain composites of porous fiber matrix and superabsorbent material are known to exhibit gel-blocking. Gel-blocking occurs when the superabsorbent material swells on contact with liquid and blocks a significant number of the capillaries present in the matrix. Such a situation is illustrated in FIG. 3. Once gel-blocking occurs, subsequent fluid surges can not move through the matrix in order to be absorbed by additional superabsorbent material located remote from the location of the fluid surges.

The inventor has discovered that by selecting the size of the superabsorbent material the effects of gel-blocking can, at least to an extent, be further minimized. Specifically, when in the form of discrete particles, at least about 50%, and preferably at least about 80% by weight, of the superabsorbent material should have a size in the unswollen condition which is greater than the median interfiber spaces (pores) of the matrix, when the matrix is in a wetted condition. That is, the size of at least about 50% of the unswollen superabsorbent particles must be greater than the median pore size of the matrix when the matrix is wet and the superabsorbent particles are not present.

When the superabsorbent material of the present invention has a dry size within the defined ranges and does not break apart into smaller units when wetted, it will, upon swelling, generally expand such that it maintains a capillary structure in the matrix. That is, rather than expanding to fill the pores as in FIG. 3, the superabsorbent expands to push the fibers apart as illustrated in FIG. 4. In this manner an open capillary structure is maintained even when the superabsorbent is in a swollen state. Maintenance of a capillary network allows the matrix in a target area (where liquid initially is applied to an absorbent structure) to be more readily dehydrated thus allowing the matrix to more readily receive the next fluid insult.

As used herein reference to the size of the superabsorbent particles refers to the size of the particles, as determined by sieve analysis according to American Society for Testing and Materials test method D-1921.

As a general rule, when the matrix is formed from the fibers described above, in the manner described above and has the densities described above, the relationship between superabsorbent particle size and the pore size of the matrix can be achieved by having at least about 50% of the superabsorbent particles with a size greater than about 100 microns, beneficially greater than about 150 microns and preferably greater than about 200 microns.

When the superabsorbent material is in the form of a fiber (having a length to diameter ratio of at least 5:1) both the length and diameter of the fiber affect gel-blocking. Specifically, when in the form of a fiber, the superabsorbent fiber may contact the matrix fibers at a number of locations along its length. As a result of these additional contacts it is not necessary for a superabsorbent fiber to meet the limitations set forth above with respect to particle size. However, as a general rule it is desireable that at least about 50 weight percent and preferably at least about 80 weight percent of the superabsorbent fibers, based on total weight of said fibers, have a geometric mean diameter of at least about 33 microns, preferably of at least about 67 microns, and a length to geometric mean diameter ratio of at least 5:1. The geometric mean diameter is the square root of the product of the major cross sectional axis and the minor cross sectional axis.

Absorbent composites were made according to Examples I-IX (including comparative examples) and tested as set forth in the following methods.

TEST METHODS

Synthetic Urine

The synthetic urine composition used herein was adjusted to more closely simulate the electrolyte composition of baby urine, namely: 0.31 g. $CaH_{4,1}(PO_4)_2 \cdot H_2O$, 0.68 g. $K H_2PO_4$, 0.48 g. $MgSO_4 7H_2O$, 1.33 g. $K_2SO_4$, 1.24 g. $Na_3PO_4 12H_2O$, 4.4 g. NaCl, 3.16 g.KCl, 2g Methyl Paraben and 5g Germall 115 as preservatives, 8.6g. urea and 0.1 g. Pluronic 10R8 per liter, using distilled water as a solvent. The components were added to 900 mls. of distilled water in the order given and each dissolved before the next component was added, and finally diluted to 1 liter. To obtain larger quantities, the above quantities were scaled-up proportionately.

Absorbency Under Load

Figure 11:
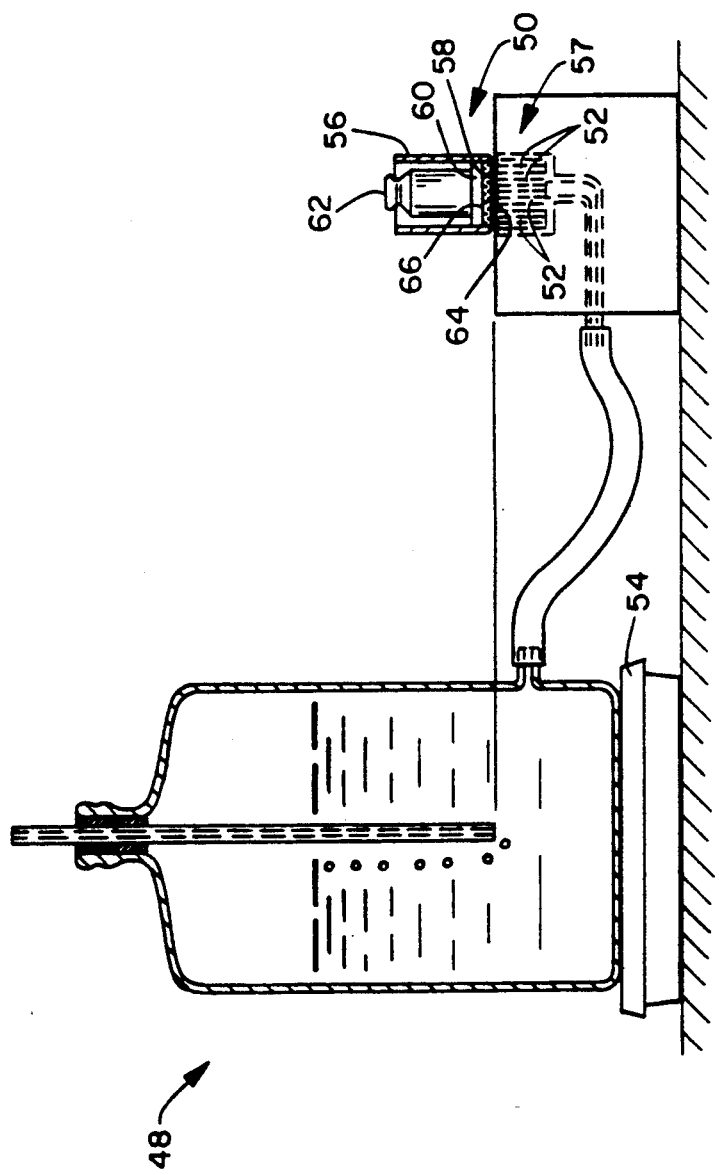
FIG. 11 is a side elevational view of an apparatus used to measure the absorbency of fluid by superabsorbent particles against an applied restraint.

Referring to FIG. 11, a Demand Absorbency Tester (DAT) 48 is used, which is similar to a GATS (Gravimetric Absorbency Test System), available from M/K Systems, Danners, Ma., as well as the system described by Lichstein in pages 129-142 of the INDA Technological Symposium Proceedings, Mar. 1974. A porous plate 57 is used having ports 52 confined within the 2.5 cm. diameter area and covered by the absorbency underload (AUL) apparatus 50. An electro balance 54 is used to measure the flow of fluid, normally 0.9 (w/w)% NaCl into the hydrocolloid particles 66. The special apparatus 50 used to contain the hydrocolloid particles is made from one inch (2.54 cm.) inside diameter thermoplastic tubing 56 machined-out slightly to be sure of concentricity and then 100 mesh stainless steel wire cloth 58 is fused on the bottom by heating the wire cloth in a flame until red hot after which the cylinder is held onto the cloth until cooled. A soldering iron can be utilized to touch up the seal if unsuccessful or it breaks. Care must be taken to maintain a flat smooth bottom and not distort the inside of the cylinder. The 4.4 g piston (60) is made from one inch diameter solid material (e.g., Plexiglas) and is machined to closely fit without binding in the cylinder 56. A standard 100 gm. weight 62 is used to provide a 21,000 dyne/sq.cm. (about 0.3 psi) restraining load which is commonly experienced in infant diapers. Unless specified otherwise, a sample corresponding to a layer of at least about 300 gsm. (0.16 g.) of granules is utilized for testing AUL. The sample is taken from granules which are pre-screened through U.S. standard #30 mesh and retained on U.S. std. #50 mesh. The particles can be pre-screened by hand or automatically with, for example, a Ro-Tap Mechanical Sieve Shaker Model B available from W. S. Tyler, Inc., Mentor Ohio.

This test is initiated by placing a 3 cm. diameter GF/A glass filter paper 64 onto the plate 57, (the paper is sized to be larger than the i.d. and smaller than the o.d. of the cylinder, to insure good contact while eliminating evaporation over the ports 52 of the DAT 48 and then allowing saturation to occur. The desired amount of particles 66 (about 0.16 g.) is weighed out on a weigh paper and placed on the wire cloth 58 at the bottom of the AUL apparatus 50. The apparatus 50 is shaken to level the granules 66 on the wire cloth 58. Care is taken to be sure no granules 66 are clinging to the wall of the cylinder 56. After carefully placing the piston 60 and weight 62 on the granules 66 in the cylinder 56, the AUL apparatus 50 is placed on the glass filter paper 64. The amount of fluid pick-up is monitored as a function of time either directly by hand, with a strip chart recorder or directly into a data acquisition or Personal Computer System.

The amount of fluid pickup measured after one hour is the AUL value, however, the rate of fluid pickup can also be measured. Two checks can be made to insure the accuracy of the instantaneous final readout. The height the piston 60 rises multiplied by the cross-sectional area of the cylinder 56 should nearly equal the amount of fluid picked up and the cylinder apparatus 50 can be weighed before and after the test, with the difference in weight equaling the fluid pick-up.

To analyze the impact of different restraining loads additional or smaller weights are utilized. Further insights are also obtained by analyzing the actual work done which is simply the height multiplied by the restraining load (or the restraining pressure in dynes/sq.cm. multiplied by the AUL (ml./g.) to yield the amount of work (ergs./g.). This is the total work done due to the particles 66 being totally restrained from moving in the X-Y plane by the cylinder 56. This restraint in the X-Y plane is the key feature of this test, since with a 300 gsm. layer the particles being restrained in the X-Y plane must expand a significant distance vertically against the restraining load in order to obtain a large AUL value.

Gel Stiffness (Shear Modulus)

The shear modulus or gel stiffness (G') is determined using pre-screened particles of from about 90 to 300 micrometers (retained on No. 170 U.S. std. sieve, passing through No. 30 U.S. std. sieve) by swelling the particles in a 100:1 solution of NaCl (0.9 w/w %) for one hour, removing the excess fluid with vacuum by spreading the gel on a Buchner funnel covered with filter paper for 3 minutes. The gel is kept in a closed container until ready for testing.

Just before placing the gel between the parallel plates of the rheometer, it is blotted on filter paper to be sure no free water is present between the particles during testing.

Testing is done on a Rheometrics, Inc. RDS II dynamic mechanical spectrometer between 25 mm. diameter parallel plates, spaced 2 mm. apart, at 1% strain amplitude, 10 radian/sec. oscillation frequency and at ambient temperature (22° C.).

Horizontal Wicking Under Load - Test Method

Figure 12:
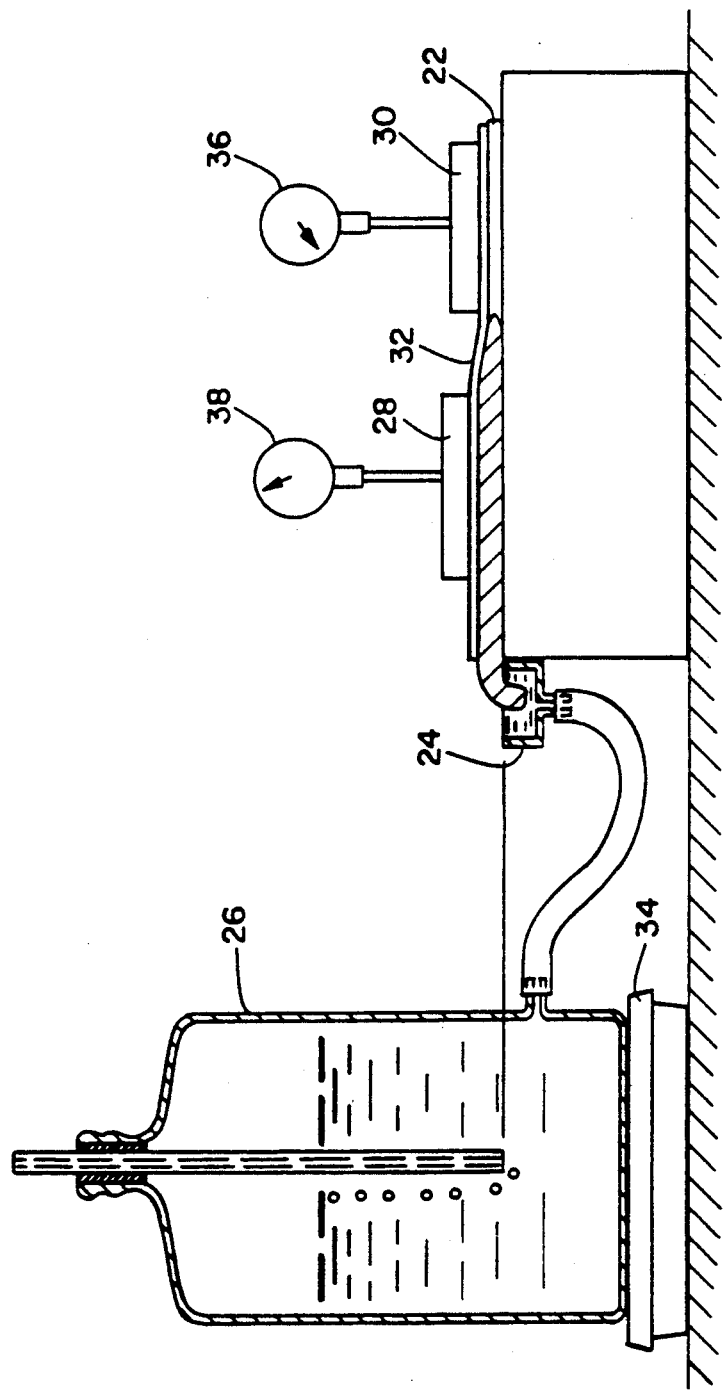
FIG. 12 is a side elevational view of an apparatus used to measure horizontal wicking of absorbent composite under an applied restraint.

Again a DAT is utilized, as in FIG. 12, except that the end of a 3"×14.5" strip of composite 22 is placed in a trough 24 fed from the fluid source 26. Weights 28 and 30 of 2700 g each are placed on a clear slab (for example Plexiglas ® having a ¼" thickness and covering the strip 22. The amount of fluid being wicked through the composite 22 is determined with an electrobalance 34. The bulk increase is indicated on the dials 36, 38 which measure these properties as a function of time. By lowering the fluid source 26, the fluid intake is periodically halted, simulating actual multiple urine insults in use. At the end of the prescribed routine i.e., 5 minutes fluid intake, 15 minutes without fluid intake (repeated 3 times), the fluid distribution is measured by quickly cutting the strip into sections, weighing these sections wet, drying them, weighing dry and correcting for the solids from the testing fluid.

Fluid-Intake and Flowback Evaluation (FIFE)

Figure 6:
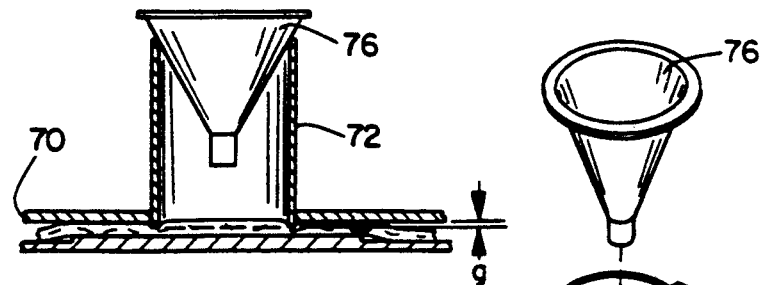
FIG. 6 is a side elevational view showing the apparatus of FIG. 5 in operation.
Figure 5:
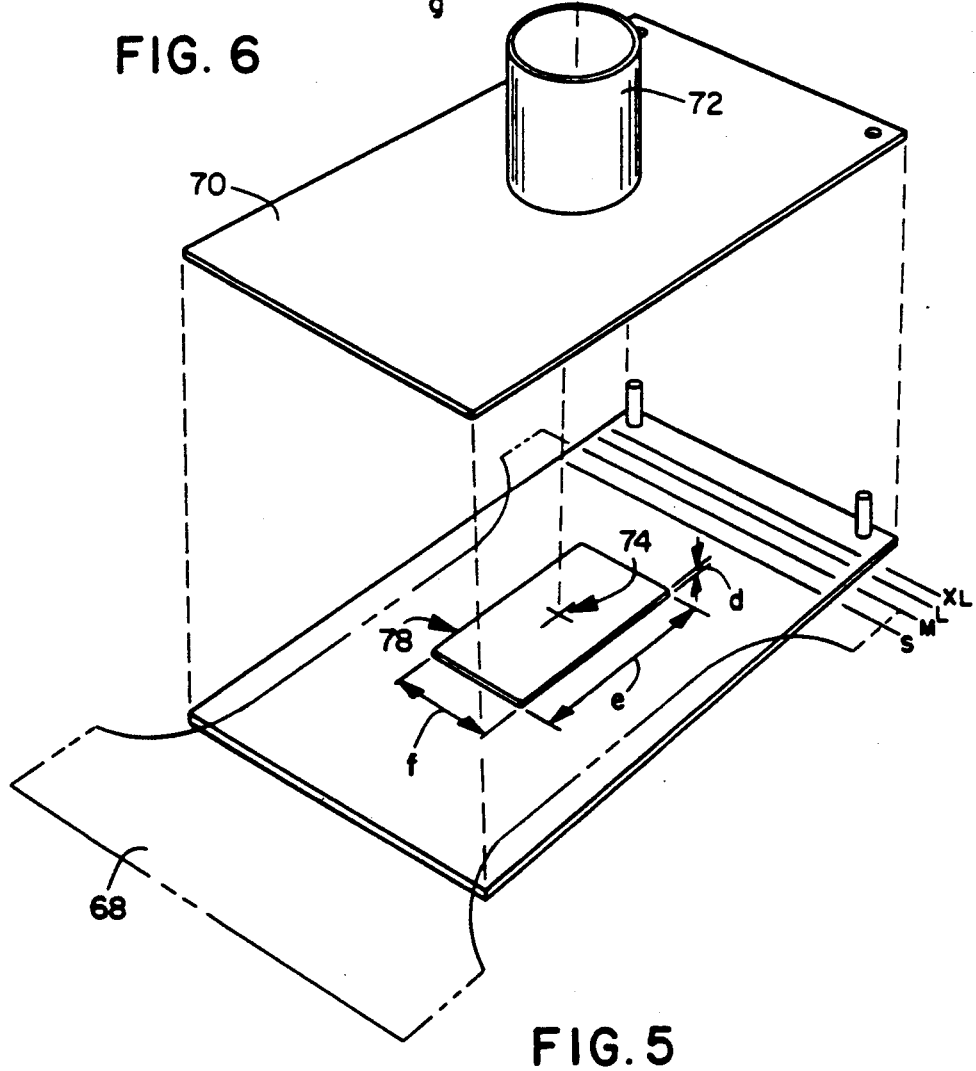
FIG. 5 is an exploded perspective view of a testing apparatus used to measure horizontal fluid intake and flowback characteristics of absorbent composites of the type described below.

The apparatus shown in FIGS. 5 and 6 is utilized for this test. The diaper (shown in phantom at 68) to be tested is prepared by cutting the leg elastic members (not shown) every 1" along their length in order to allow the sample to lie flat. The absorbent composite may be tested either alone or sandwiched between facing and backing sheets utilizing 2-sided tape to fasten the elements together. Sample dimensions, weight and density profile of the sample, amount of composite per sample, as well as the facing and backing materials, must be controlled as appropriate to obtain valid results. Data reported herein were obtained with 5"×15" rectangular absorbent batts alone.

The sample 68 to be tested is placed flat and smooth under an 880g cylinder plate assembly 70 such that the cylinder 72 which has a 5.1 cm i.d., ends up in a designated location 74. For example, 4-½" from the edge of the composite for small (s), 5" from the edge for medium (m), 5-½" for large (l) and 5-¾" for extra large (×l) diapers was used. Under the sample 68 is a raised platform 78 which is ½" high (d) × 6" long (e) × 3" wide (f). Also, the cylinder 72 extends a distance (g) of about 1/32" below the cylinder plate assembly 70.

A specified amount of synthetic urine (e.g. 60, 80 and 100 ml., respectively, for small, medium and large diapers) is poured through the funnel 76 on top of the cylinder 72. The time elapsing between the first fluid contact with the sample and the time when fluid disappears into the sample is measured with a stop watch. One minute after the initial fluid insult is imbibed, a second insult of the same size is introduced. The time to imbibe the fluid is measured as for the first insult.

Referring to FIGS. 9 and 10, one minute after the second insult is imbibed, the sample 68 is placed on a vacuum apparatus 80 and covered with blotter paper 82 together with liquid impervious latex sheeting 84. A 35,000 dyne/sq. cm (about 0.5 psi) vacuum pressure is then applied to suck the impervious latex sheeting 84 onto the blotter 82 and sample 68 for two minutes. The increase in weight of the blotter paper 82 represents the flowback.

Within one minute after completion of the flowback, a third fluid insult is introduced and timed. The fluid-intake time then is the number of seconds for the prescribed amount of fluid (80 ml for the results quoted herein) to enter the sample.

Vertical-Fluid Intake and Flowback Evaluation (V-FIFE)

Figure 7:
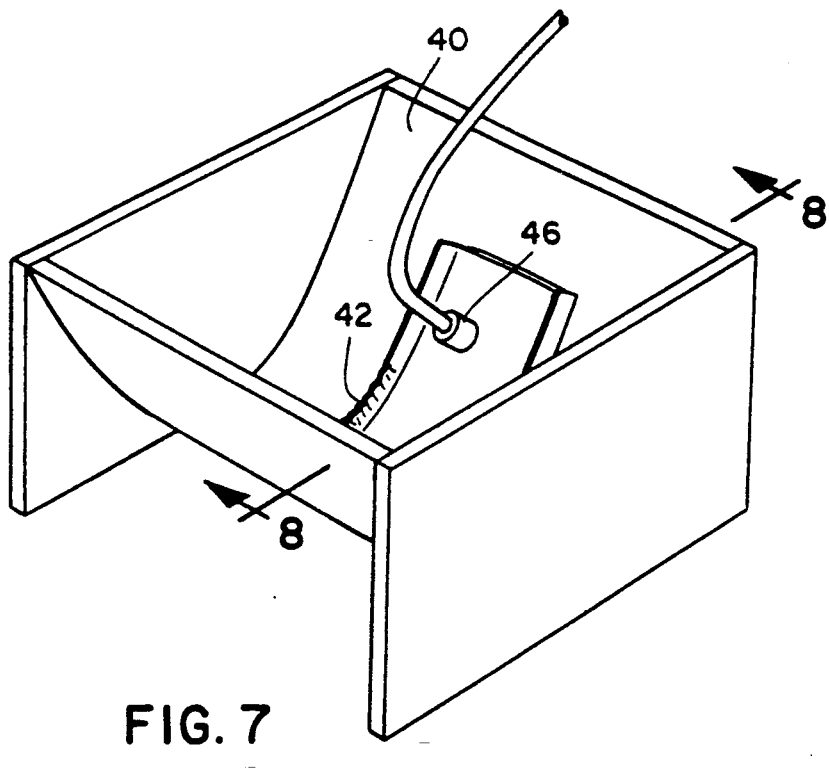
FIG. 7 is a perspective view of a testing apparatus used to evaluate fluid intake and flowback of absorbent composites of the type described herein, when the composites are in a normal configuration of use.
Figure 8:
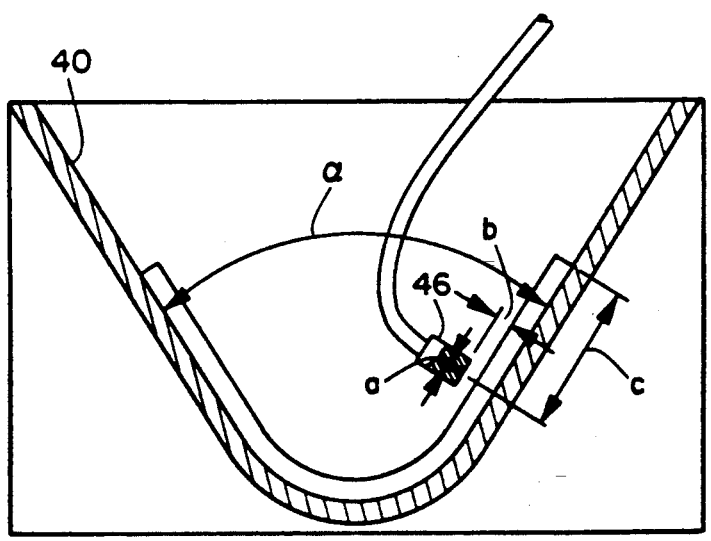
FIG. 8 is a cross-sectional view of FIG. 7.

Referring to FIGS. 7 and 8, the absorbent structure is placed in a trough 40 with an included angle, alpha of 60°, such that all "runoff" is contained on the bodyside proximity of the absorbent structure using suitable dams 42 along the sample edges. The total time to imbibe the insult is measured. Fluid is delivered from a nozzle 46 having 4 mm. diameter (a) which is attached to a peristaltic pump equipped with a pulse suppressor. The nozzle is placed a distance (b) of 6 mm. from the absorbent surface, a distance (c) of about 6.3 cm from the end of the composite and at a perpendicular angle. Fluid is dispensed at an average rate of 12 ml./sec. for 5 seconds during each insult (total 60 ml).

The fluid volume per insult (60 ml) is divided by the time elapsed between initial fluid contact and disappearance beneath the absorbent surface to determine the fluid intake rate. Samples are allowed to equilibrate 15 minutes between insults. For the data utilized herein, no flowback evaluation took place between the 2nd and 3rd insult, as in the FIFE test.

Multiple Insult Demand Absorbency Test (MIDAT)

A piece of absorbent composite 68 mm. in diameter was placed over a single 3 mm. port of a DAT (as in the AUL test, FIG. 11), with about a 17,000 dyne/sq. cm. (about 0.25 psi) load placed on the sample. After 3 g/g. of fluid was absorbed, a valve was closed to prevent transfer of additional fluid for 15 minutes. The valve was then opened until 6 g/g. was reached, at which time it was closed for another 15 minutes, then opened until 9 g/g. was imbibed. After another 15 minutes, the valve was opened to obtain the final fluid intake rate.

By inspection of a graph showing fluid uptake, the time to reach 3, 6 and 9 g/g. can be compared.

Permeability

Figure 13:
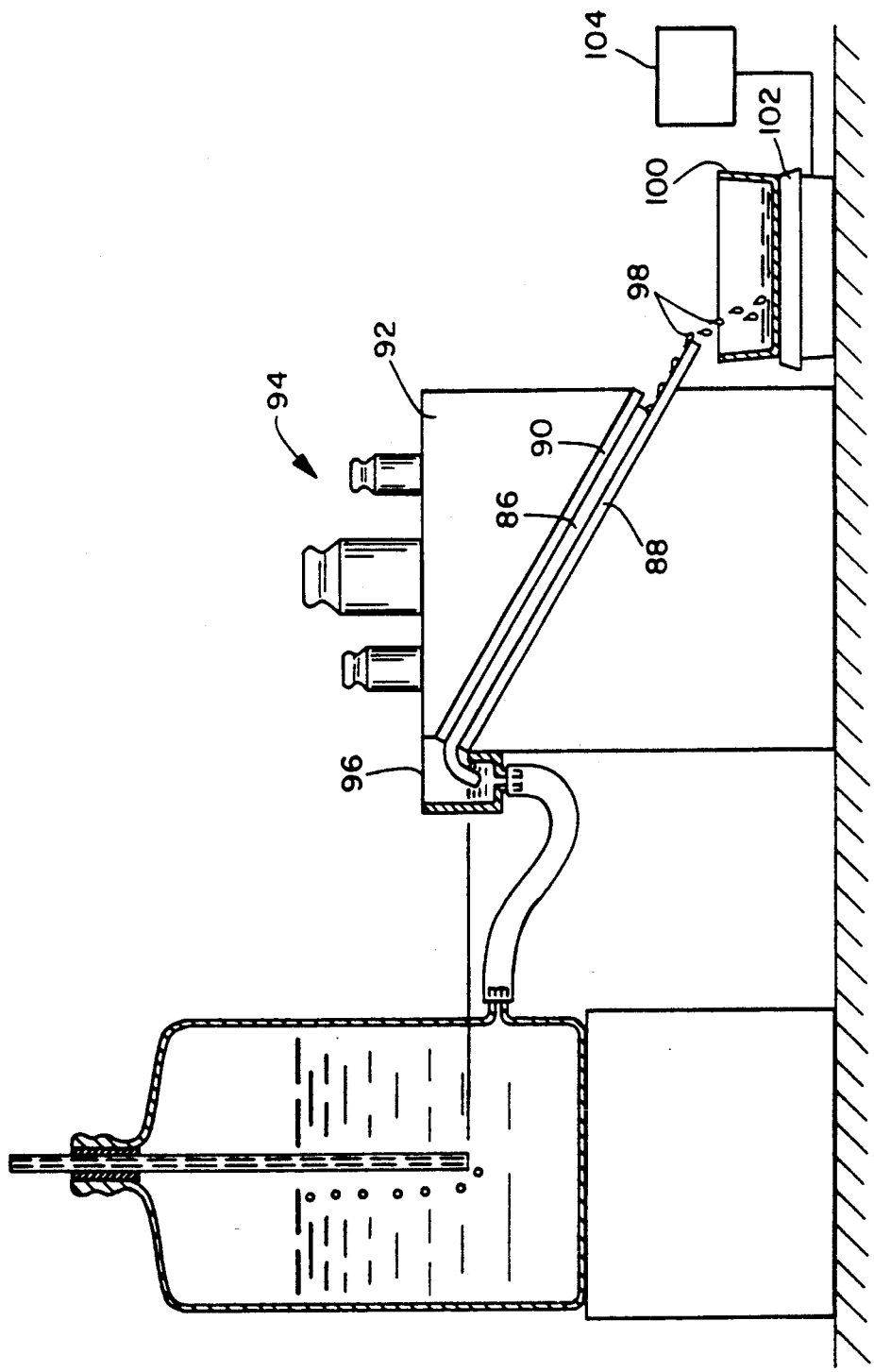
FIG. 13 is a side elevational view of an apparatus used to measure the permeability to fluid of absorbent composites.

Permeability of the saturated absorbent composite structures was determined by constructing a siphon, as shown in FIG. 13, wherein the sample 86 is supported by a nonwettable teflon-coated plate 88 inclined at an angle of 45°. A second nonwettable plate 90 with a platform 92 for receiving weights 94 thereon was placed over the sample, being restrained from sliding by an anchor string 96. A weight of 964 gms. was utilized to provide 21,000 dynes/cm$^2$ (about 0.3 psi) of pressure perpendicular to the sample. The amount of fluid 98 passing through the sample was collected in a pan 100 resting on an electro balance 102 connected to a strip chart recorder 104. The amount of fluid passing through the sample per unit time after an equilibrium flow rate is established is proportional to the in-plane permeability which, in turn, is related to the degree of openness of the absorbent composite structure and a direct measure of the ability of the sample to conduct fluid.

EXAMPLE I

Absorbent composites were made according to the teachings of U.S. Pat. No. 4,699,823 to Kellenberger et al., the entire disclosure of which is hereby incorporated by reference and relied upon, with the superabsorbent material (hydrocolloid particles) disposed in a Z-direction gradient in the batt. Commercially available facing and backing sheets were used and the absorbent composite included hydrocolloid particles (now sold under the designation IM5000), PA200, lot no. U702642, obtained from Hoechst Celanese Corporation. The hydrocolloid is a crosslinked sodium salt of poly(acrylic acid). The absorbent composite had a center basis weight of about 850 gsm with about 80% of the SAP in the center 4 inches of the diaper.

EXAMPLE II

Absorbent composites were made according to the process described in Example I, only using a hydrocolloid sold as IM1500P, lot no. 70982B050, by Hoechst Celanese, Portsmouth, Va. The hyrocolloid is a starch grafted crosslinked sodium salt of poly(acrylic acid). The absorbent composite had the same basis weight and SAP distribution as Example I.

EXAMPLE III

Absorbent composites were made by the method described in U.S. Pat. No. 4,650,127 to Radwanski et al., the entire disclosure of which is hereby incorporated by reference and relied upon, with starch graft hydrocolloid particles obtained from Hoechst Celanese identified as IM1500P sample number S-73-990-01 dispersed homogenously in the airlaid batt of fibers by a continuous stream. The hydrocolloid is a starch grafted crosslinked sodium salt of poly(acrylic acid). The hydrocolloid used in the composite had physical properties which were the same as that used in Example I. The absorbent composites formed had a basis weight of about 1,000 gsm.

EXAMPLE IV

Absorbent composites were made according to Example III, using a hydrocolloid sold under the name Drytech 532, lot no. 87022118, by The Dow Chemical Company of Midland, Mich. The hydrocolloid is a crosslinked sodium salt of poly(acrylic acid). The absorbent composites formed had a basis weight of about 1,000 gsm.

EXAMPLE V

Absorbent composites were made according to Examples III and IV with a basis weight of about 500 gsm and a uniform distribution of superabsorbent (hydrocolloid) particles in the batt. The hydrocolloid used was obtained from Hoechst Celanese Corporation under the designation IM5000P, with a sample number S-93-1171-01. The hydrocolloid is a crosslinked sodium salt of poly(acrylic acid).

EXAMPLE VI

Absorbent composites were made according to Example V, using hydrocolloid obtained from the Dow Chemical Company under the designation Drytech 532, Lot No. 861014C. The hydrocolloid is a crosslinked sodium salt of poly(acrylic acid).

EXAMPLE VII

Absorbent composites were made in accordance with the method of Examples I and II, using a hydrocolloid obtained from the Dow Chemical Company under the designation Drytech 533, lot no. 87040221. The hydrocolloid is a crosslinked sodium salt of poly(acrylic acid).

EXAMPLE VIII

Absorbent composites were made according to Example I, using hydrocolloid particles obtained in an agglomerated form as IM5000, lot no. U706607 from Hoechst Celanese Corporation, Portsmouth, Va. The hydrocolloid is a crosslinked sodium salt of poly(acrylic acid). This hydrocolloid tended to de-agglomerate resulting in less favorable performance when tested than did the nonagglomerated IM5000 of Example I. It is believed that the small, de-agglomerated particles of Example VIII impair performance by clogging the interfiber spaces and the spaces between the particles, thereby reducing permeability of the composite. It is further believed that results observed with Example VIII indicate the significance of the particle size distribution in performance of the composite.

EXAMPLE IX Absorbent composites were made according to Example I, using hydrocolloid particles obtained as IM1500P, lot no. 71991A641 from Hoechst Celanese Corporation, Portsmouth, VA. The hydrocolloid is a starch grafted crosslinked sodium salt of poly(acrylic acid). Example IX represents a prior art comparative control versus Example VIII. Results indicate agglomerated IM5000 (Example VIII) functions at parity with IM1500 (Example IX).

SUMMARY OF TEST RESULTS

Figure 14:
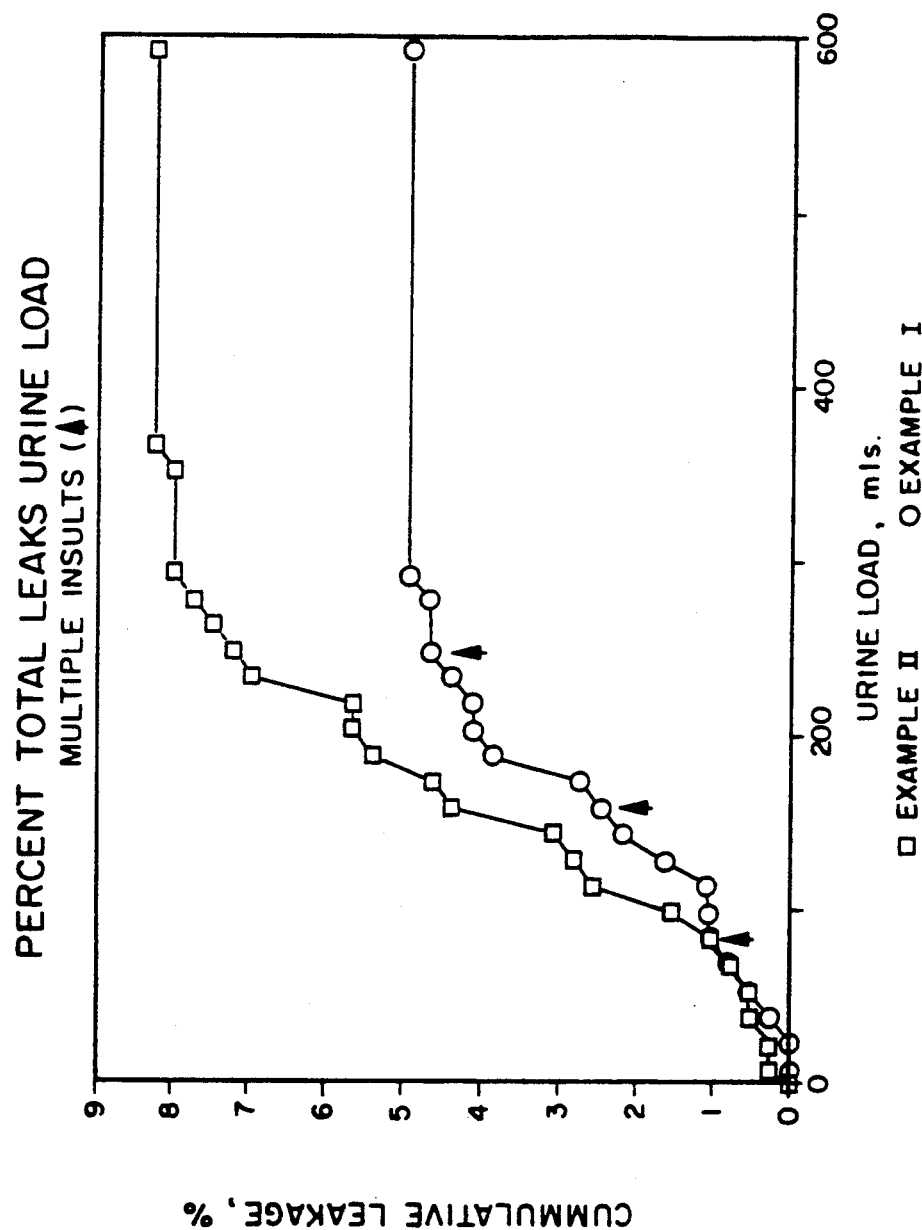
Figure 15:
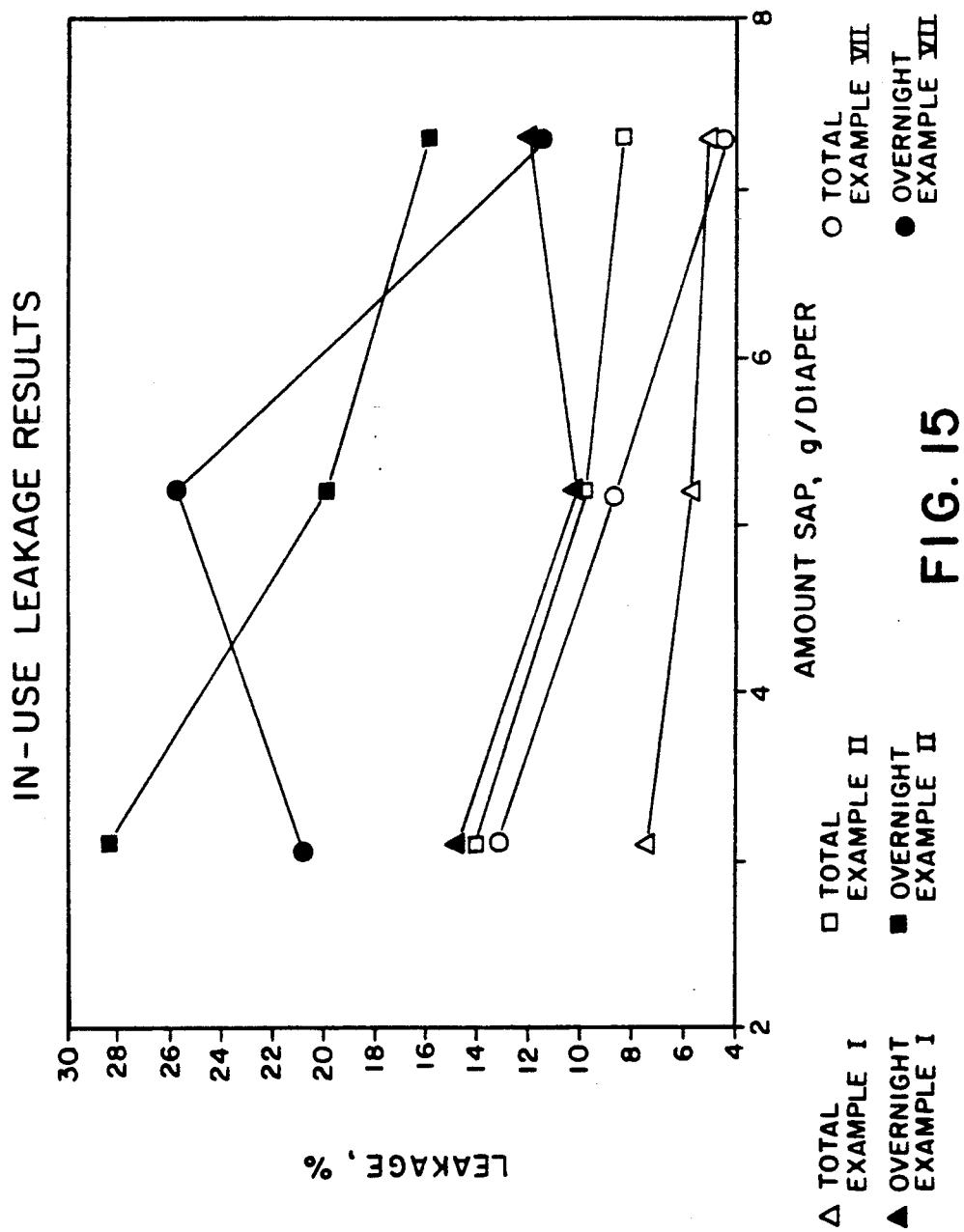

As shown by the graphs of FIGS. 14, 15, and 22, whole diapers of the general configuration discussed and shown in conjunction with FIG. 1, and having absorbent composites made according to the Examples indicated, were tested on infants and the percentage of leaks was determined by the ability of the diaper to contain urine without overflowing onto and soiling outer clothing. As shown in the graph of FIG. 14, lower leakage rates are apparently attributable to the preferred diaper being able to better absorb and contain urine upon the second and third, rather than only the first urine surge or insult. It is estimated that these surges correspond to the average bladder capacity of the infants being tested. The purpose of this test was to qualitatively confirm the results of the experimental measurements obtained according to the test methods discussed herein. These in-use test results showed significantly improved leakage reduction in diapers having absorbent composites with hydrocolloid particles having a higher AUL where the average amount of hydrocolloid per diaper was in the range of 3 to 7 grams. Table A, immediately below, summarizes the percentage of leaks observed. Consistency of the results indicates that no pattern exists to indicate any interaction with different loadings of SAP. (Note, Example VII's 7 gpd. total leakage results appearing better than Example I's 7 gpd. total leakage results is attributable to normal experimental variability.)

This data clearly demonstrates the desirability of employing a relatively high AUL superabsorbent material. As the AUL of the superabsorbent material increases the performance (as measured by leakage) of a diaper employing the superabsorbent material similarly increases. This relationship between performance and AUL has not heretofor been recognized.

TABLE A

| Example No. | IN-USE LEAKAGE RESULTS | | | | |
|---|---|---|---|---|---|
| | % Total Leaks | | | Overnight Leaks | |
| | g/Diap. | | Avg. | Avg. | |
| I | 3 | | 7.4 | 14.7 | |
| I | 5 | | 5.8 | 6.1 | 10.1 | 12.3 |
| I | 7 | | 5.1 | | 12.0 | |
| VII | 3 | | 12.6 | | 20.7 | |
| VII | 5 | | 8.2 | 8.0 | 21.2 | 16.4 |

TABLE A-continued

| Example No. | IN-USE LEAKAGE RESULTS | | | |
|---|---|---|---|---|
| | % Total Leaks | | Overnight Leaks | |
| | g/Diap. | Avg. | Avg. | |
| VII | 7 | 3.1 | 7.4 | |
| II | 3 | 14.2 | 28.4 | |
| II | 5 | 9.8 | 10.8 | 20.0 | 21.4 |
| II | 7 | 8.4 | | 16.0 | |

Figure 18:
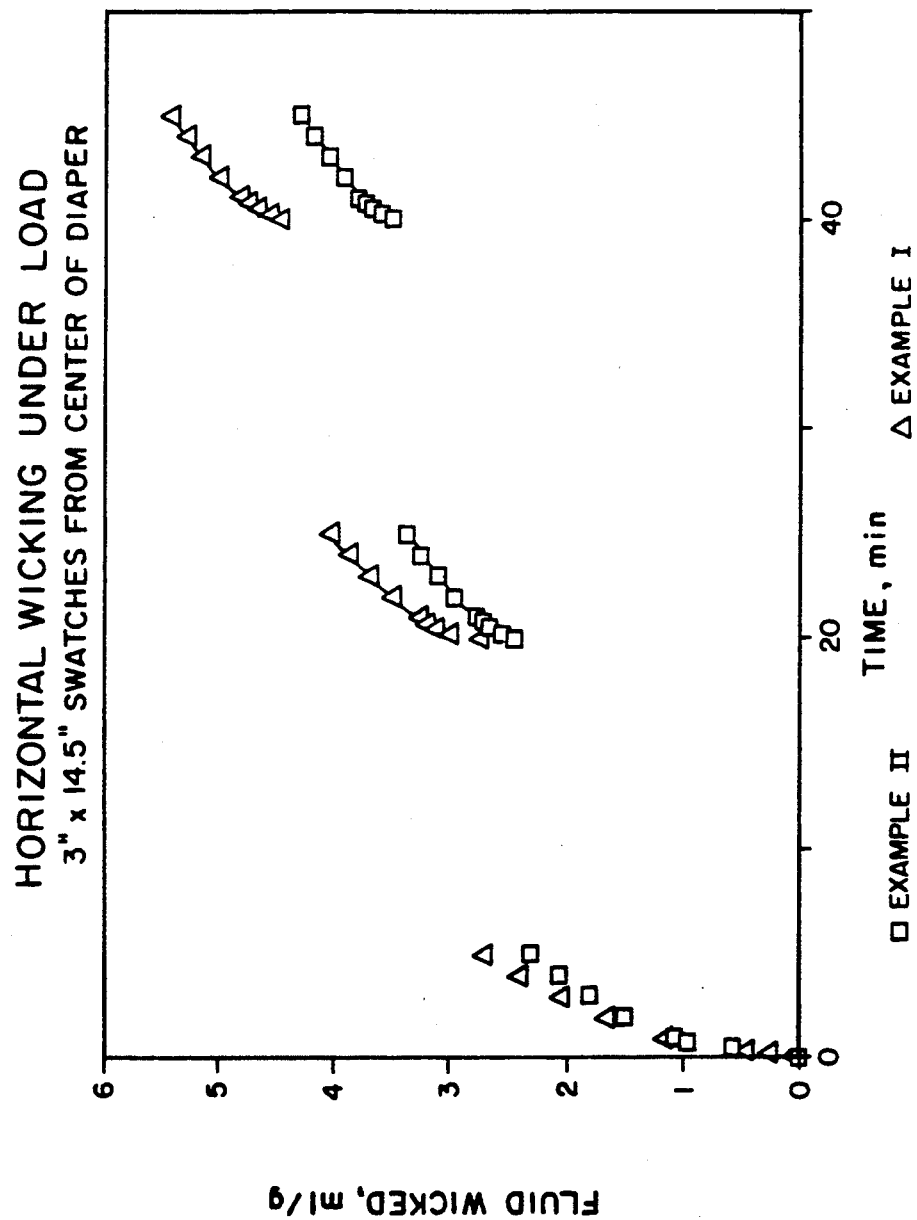

Samples of diaper comprising the sandwiched absorbent composite having facing and backing sheets attached thereto, were subjected to the Horizontal Wicking Under Load test. Fluid uptake capacity was measured for 5 minutes (three repititions, 15 minutes apart) under an applied load of 0.33 psi. The amount of fluid uptake is shown on the graph in FIG. 18 and the fluid wicking distance in FIG. 19. The test results indicate that a reduction in wicking occurred due to swelling of the hydrocolloid particles and, consequently, the clogging of the pores in the samples of Example II. This phenomenon is fully confirmed by the permeability tests discussed below, even though no significant differences in bulk change between composites having high vs. low AUL hydrocolloids were observed during these tests. The test results in FIG. 21 further show that those Examples using higher AUL hydrocolloids perform a greater amount of work producing a more open structure, resulting in greater wicking rates, than the lower AUL Examples.

FIG. 5 shows the apparatus used to measure horizontal fluid intake and flowback of composites subjected to loads of approximately 0.1 psi (about 7,000 dynes per square centimeter). The test results indicated that the average fluid intake values for Examples containing high AUL hydrocolloids exhibited a 15-20% improvement on the second insult over those Examples containing a lower AUL hydrocolloid for composite densities of about 0.15 grams/cubic centimeter. A lower scale second insult improvement of about 5% was seen for higher AUL composites at densities of about 0.10 grams/cubic centimeter. However, a 20% improvement was seen on the third fluid insult regardless of density in the range from about 0.10 to 0.15 grams per cubic centimeter.

The test shown in FIGS. 7 and 8 endeavors to simulate actual product alignment in use while multiple insults of fluid are delivered to the absorbent composite, measuring the rate of fluid imbibed. The results shown in FIG. 20 indicate that the rate of fluid uptake increased, even with increased hydrocolloid particle concentration, for those examples having composites containing relatively higher AUL hydrocolloids. Significantly, the rate of uptake on the fourth fluid insult closely resembled the rate for the first insult for absorbent composites containing high AUL hydrocolloids.

Figure 16:
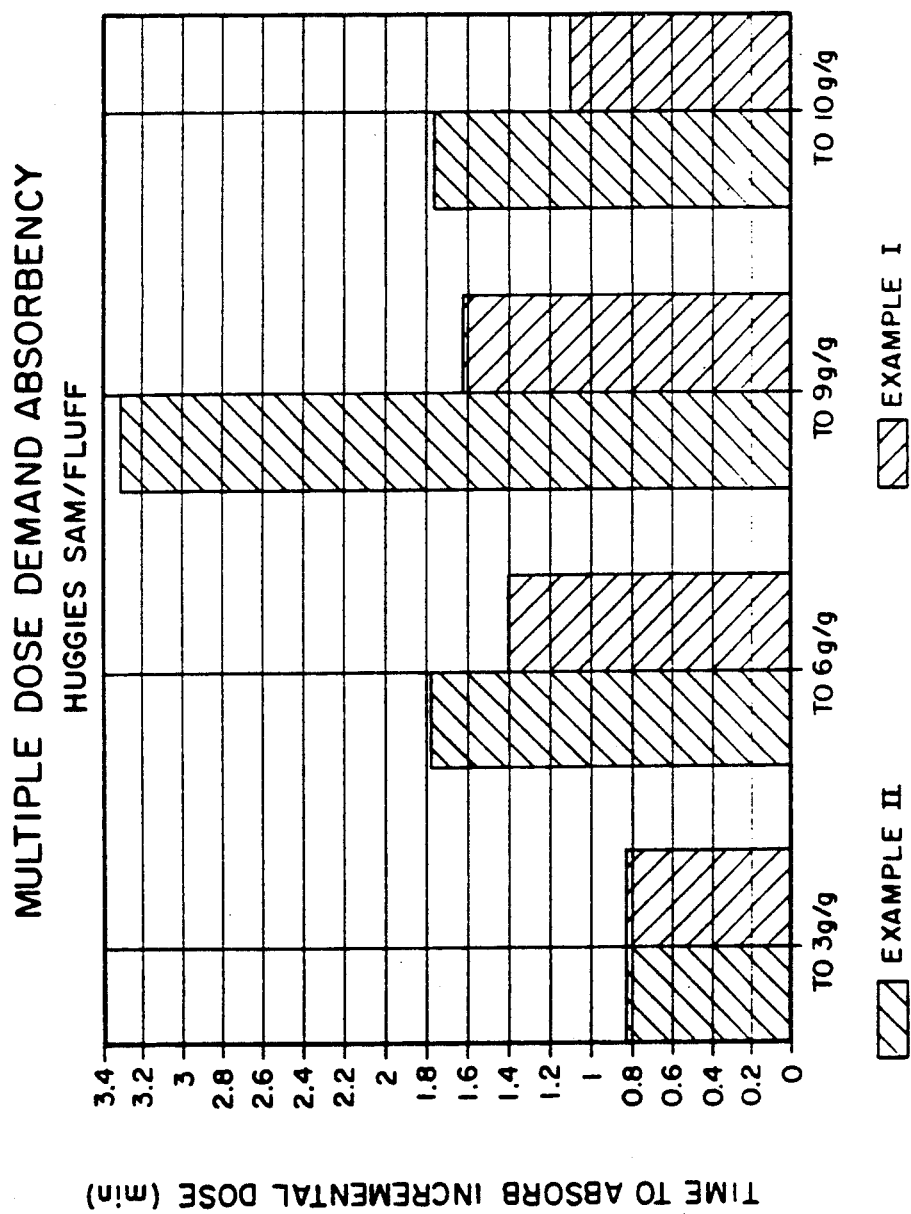
Figure 17:
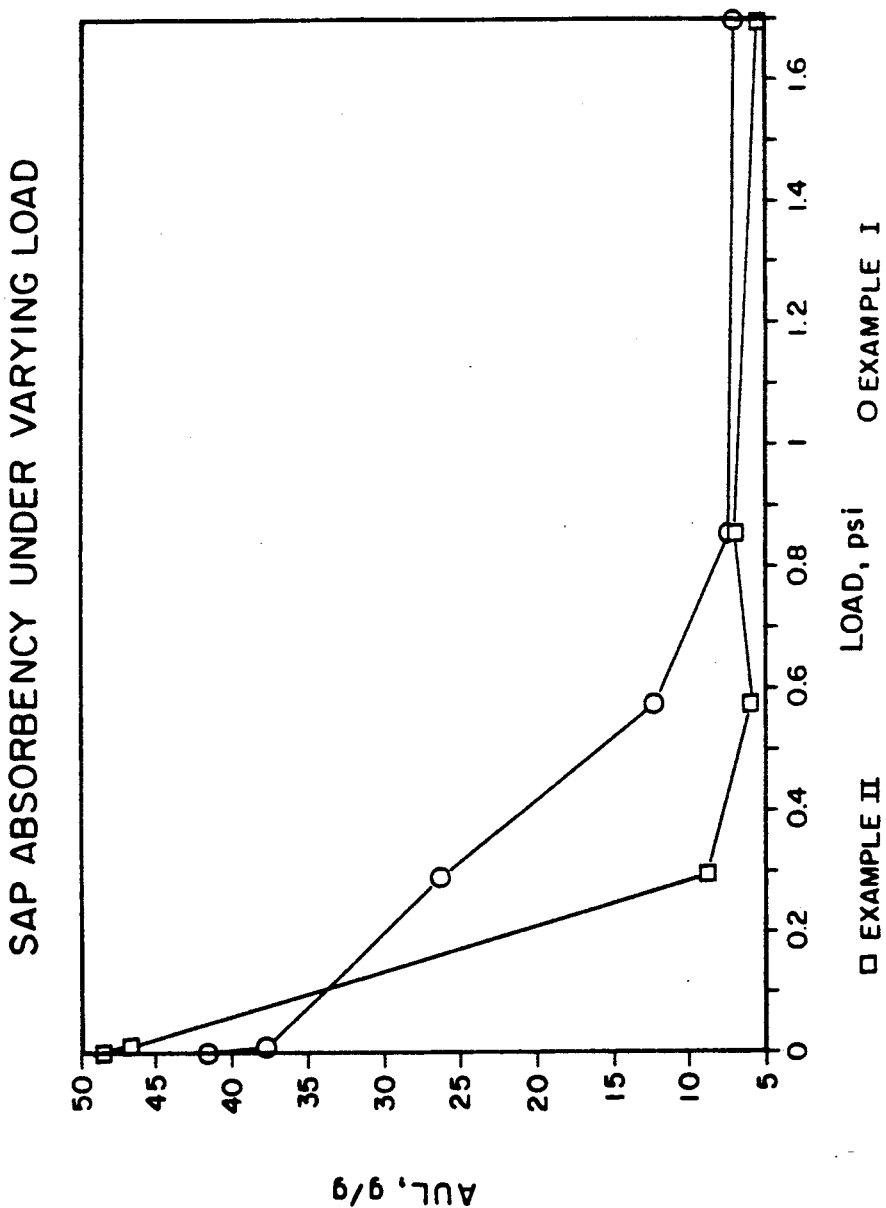

The Multiple Insult Demand Absorbency Test (MIDAT) was employed to simulate the time between actual fluid insults in diaper use, wherein the fibrous matrix of the absorbent composite collapses when wet about the hydrocolloid particles. As shown by the results depicted in FIG. 16, these Examples comprising hydrocolloids with relatively higher AUL's imbibe faster during multiple fluid insults. This quality again correlates to better diaper performance in terms of less urine leakage. As shown graphically by the results summarized in FIGS. 17 and 21, Examples containing the relatively higher AUL hydrocolloid perform a significantly higher and more consistent amount of work against an applied load of up to about 1.0 psi during the time that multiple fluid insults are imbibed. These results are also summarized in Table B below.

TABLE B

| | | AUL & WORK VS APPLIED LOAD | | | |
|---|---|---|---|---|---|
| | | SAP FROM EXAMPLE I | SAP FROM EXAMPLE II | | |
| Pressure | | AUL* | WORK | AUL* | WORK |
| PSI | (Dynes/Cm$^2$) | ml/g | ergs/g | ml/g | erg/g |
| 0 | 0 | 42 | 0 | 48 | 0 |
| 0.012 | 850 | 38 | 32,300 | 47 | 39,950 |
| 0.30 | 20,700 | 26 | 538,200 | 9 | 186,300 |
| 0.56 | 38,600 | 13 | 501,800 | 8 | 308,800 |
| 0.85 | 58,600 | 8 | 468,800 | 7 | 410,200 |
| 1.7 | 117,100 | 8 | 936,800 | 6 | 702,600 |

*Value determined based on a single measurement.

Referring to FIG. 13, the fluid flow rate through a sample of absorbent composite, acting as a syphon, was measured as an approximate restraining force of 0.3 psi was applied to the sample in order to evaluate the fluid permeability (ability to conduct fluid) of the sample indicating the degree of clogging or openness of the matrix structure. Pores that were more open gave less resistance to flow through the composite, hence, high flow rate under the driving force of gravity. The results shown immediately below indicate that those Examples containing the relatively higher AUL hydrocolloid exhibited greater permeability than those containing relatively lower AUL hydrocolloids.

| Example # | Permeability (ml/min.) |
|---|---|
| I | 13 |
| II | 8 |
| V | 8 |
| VI | 6 |

Particle Size Distribution

Table C summarizes the particle size distribution of those hydrocolloid particles used in Examples I-IX (including comparative examples). When examined in light of the test results discussed below, SAP particle size is a significant parameter affecting performance of the hydrocolloids in the absorbent composites.

agglomerated vs. nonagglomerated hydrocolloid, when wet, significantly affects the percent leakage observed.

The agglomerated hydrocolloid of Example VIII, when subjected to the AUL test, exhibited a lower AUL when tested than did the same hydrocolloid in a nonagglomerated form (Example I). However, when a lesser SAP amount, for example, a monolayer of the agglomerated hydrocolloid particles (Example VIII), was used for the AUL test, AUL values were obtained which were comparable to those for Example I suggesting functional equivalence. However, the leakage comparison, FIG. 22, demonstrates only functional equivalence to prior art (Example II) hydrocolloids. These results indicate the small particles breaking off the agglomerates are filling/plugging the capillary structure in actual use and in the normal AUL test described in the Test Method section.

Hydrocolloid particles which have been found appropriate for use in absorbent composites of the present invention comprise a size distribution in a range from about 100 to about 1000 micrometers and preferably from about 200 to about 850 micrometers, as measured using U.S. Standard Mesh sieves. Significantly, the fibrous matrix having the aforementioned particle sizes is pushed apart as soon as the particles begin to swell, that is, a majority of the particles, as they begin to swell, will have a size which is larger than the interfiber spaces which were occupied by the particles when the fibers were first wetted, enabling the particles with a high AUL to push the fibrous matrix of the web apart in the direction of the web thickness (FIG. 4). In comparison, smaller particles merely expand and fill the pores without being given the opportunity to exert the necessary work to force the fibers apart. Examples containing hydrocolloid particles which are equivalently-sized but possess a relatively lower ability to absorb under load (AUL) functioned differently, they deform thus not opening flow channels (FIG. 3).

Therefore the use of particles having a smaller size distribution outside the appropriate specified range does not provide a sufficient opportunity for the particles to perform work against a restraining force. Accordingly, it has been determined that at least about 50% and preferably at least about 80% by weight of the dry particles must have a size greater than the median pore size of said porous fiber matrix when wet and when the superabsorbent particles are not present.

TABLE C

| SUMMARY OF PHYSICAL DATA (EXAMPLES I-IX) SUMMARY OF HYDROCOLLOIDS USED IN EXAMPLES I-IX | | | | | | | | | |
|---|---|---|---|---|---|---|---|---|---|
| | Ex. I | Ex. II | Ex. III | Ex. IV | Ex. V | Ex. VI | Ex. VII | Ex. VIII | Ex. IX |
| Abs. UnderLoad$^1$ ml/g | 27 | 10 | 26 | 7 | 26 | 7-10 | 22 | 16 | 11 |
| Gel Stiffness (G') (10$^3$ dynes/sq. cm) | 40 | 20 | 44 | 15-20 | 42 | 15-20 | 39 | 30 | 24 |
| Particle Size Distr. (% by wt.)* | | | | | | | | | |
| 850 micrometers | 2.5 | 0.8 | 3.5 | 0.8 | 0.3 | 0.6 | 0.4 | 0.2# | 0.9 |
| 600-850 micrometers | 25 | 17 | 19 | 15 | 14 | 15 | 20 | 20 | 17 |
| 300-600 micrometers | 33 | 31 | 42 | 41 | 45 | 39 | 44 | 57 | 39 |
| 90-300 micrometers | 29 | 36 | 35 | 41 | 36 | 38 | 31 | 24 | 33 |
| 45-90 micrometers | 7.5 | 10.9 | 0.14 | 3.0 | 4 | 6.2 | 4.6 | 0 | 7 |
| less than 45 micrometers | 2.5 | 5.0 | 0.12 | 0.1 | 1.3 | 0.9 | 0.2 | 0 | 3.5 |

*10 min. in Ro-Tap Shaker using U.S. std. sieve #'s 20, 30, 50, 170 & 325.
Fines agglomerated together and onto larger particles with bonds which break when wetted, de-agglomerating the particles.
$^1$Values determined are the average of at least three determinations. Individual determinations may be higher or lower than the stated value. Average value is believed to be more representative of the actual value.

The comparative data of FIG. 22 vs. the comparative data of FIG. 15 shows that particle size distribution of The median pore size of nonwoven fibrous webs, including fluffed pulp batts as taught herein, can be determined for example by using the method taught by Burgeni, et al. in the *Textile Research Journal*, Vol. 57 at pages 356-366 (May 1967), wherein determination of the equivalent pore diameters for both compressed and uncompressed air-laid Kraft pulp fluff batts is detailed.

Another factor besides the particle/pore size relationship is that greater numbers of particles having size distributions smaller than those contemplated by the invention are present in the fibrous matrix, thereby filling more of the pores thereof and, consequently, reducing fluid permeability of the absorbent composite. Illustratively, the agglomerated hydrocolloid particles used in Example VIII break up when wetted into smaller-sized particles, resulting only in the composite performing at parity with the prior art, as shown in FIG. 22, compared with the improved results obtained with Example I (FIG. 15).

What is claimed is:

1. An absorbent composite comprising a porous fiber matrix and an amount of superabsorbent material present in said porous fiber matrix, wherein said superabsorbent material can absorb at least 27 milliliters of an aqueous solution of sodium chloride containing 0.9 weight percent, sodium chloride, per gram of superabsorbent material while under a restraining pressure of at least 21,000 dynes per square centimeter, provided that, when said superabsorbent material is in the form of discrete particles, at least about 50%, by weight, of said superabsorbent material has a size greater than the median pore size of said porous fiber matrix when wet.

2. The absorbent composite according to claim 1, wherein the porous fiber matrix is formed from wood pulp fluff.

3. The absorbent composite according to claim 1, wherein the absorbent composite has a density of from about 0.03 to about 0.4 grams per cubic centimeter.

4. The absorbent composite according to claim 3, wherein the absorbent composite has a density of from about 0.1 to abut 0.15 grams per cubic centimeter.

5. The absorbent composite according to claim 1, wherein the composite comprises the superabsorbent material in an amount of from about 5 to about 80 weight percent based on total weight of the absorbent composite.

6. The absorbent composite according to claim 5, wherein the composite comprises the superabsorbent material in an amount of from about 10 to about 60 weight percent, based on total weight of the absorbent composite.

7. The absorbent composite according to claim 1, wherein the superabsorbent material is in the form of discrete particles.

8. The absorbent composite according to claim 7, wherein at least about 50%, by weight, of the superabsorbent material has a particle size of at least about 100 microns.

9. The absorbent composite according to claim 7, wherein at least about 50%, by weight, of the superabsorbent material has a particle size of at least about 150 microns.

10. The absorbent composite according to claim 1, wherein the superabsorbent material is in the form of fibers having a length to diameter ratio of at least 5:1, further wherein at least about 50%, by weight, of said superabsorbent fibers have a geometric mean diameter of at least about 33 microns.

11. The absorbent composite according to claim 10, wherein at least about 50%, by weight, of said superabsorbent fibers have a geometric means diameter of at least about 67 microns.

12. The absorbent composite according to claim 7 wherein at least about 80%, by weight, of said superabsorbent material has a size greater than the median pore size of said porous fiber matrix when wet.

13. The absorbent composite according to claim 12, wherein at least about 50%, by weight, of the superabsorbent material has a size of at least about 100 microns.

14. An absorbent composite comprising a porous fiber matrix and an amount of superabsorbent material present in said porous fiber matrix, wherein said porous fiber matrix comprises at least about 3%, by weight, based on porous fiber matrix weight, of a synthetic polymeric fiber, and wherein said superabsorbent material can absorb at least about 24 milliliters of an aqueous solution of sodium chloride containing 0.9 weight percent, sodium chloride, per gram of superabsorbent material while under a restraining pressure of at least 21,000 dynes per square centimeter provided that, when said superabsorbent material is in the form of discrete particles, at least about 50%, by weight, of said superabsorbent material has a size greater than the median pore size of said porous fiber matrix when wet.

15. The absorbent composite according to claim 14 wherein the absorbent composite has a density within the range of from about 0.03 to about 0.4 grams per cubic centimeter.

16. The absorbent composite according to claim 14 wherein the absorbent composite comprises the superabsorbent material in an amount of from about 5 to about 80 percent by weight, based on total weight of the absorbent composite.

17. The absorbent composite according to claim 14 wherein the superabsorbent material is present in the form of discrete particles and wherein at least about 50% by weight, of the super-absorbent particles have a particle size of at least about 100 microns.

18. The absorbent composite according to claim 17 wherein at least about 80%, by weight, of said superabsorbent material has a size greater than the median pore size of said porous fiber matrix, when wet.

19. The absorbent composite according to claim 18 wherein the superabsorbent material is present in the form of discrete particles having a size of at least about 100 microns.

20. A diaper, said diaper comprising:
a liquid-permeable facing material;
an absorbent composite adjacent said liquid-permeable facing material, said absorbent composite comprising a porous fiber matrix and an amount of a superabsorbent material present in said porous fiber matrix, wherein said superabsorbent material can absorb at least 27 milliliters of an aqueous solution of sodium chloride containing 0.9 weight percent sodium chloride, per gram of superabsorbent material while under a restraining pressure of at least 21,000 dynes per square centimeter, provided that, when said superabsorbent material is in the form of discrete particles, at least about 50%, by weight, of said superabsorbent material has a particle size greater than the median pore size of said porous fiber matrix when wet; and
a liquid-impermeable backing material adjacent said absorbent composite and located opposite said liquid-permeable facing material.

21. The diaper according to claim 20 wherein the porous fiber matrix is formed from wood pulp fluff.

22. The diaper according to claim 22 wherein the absorbent composite has a density of from about 0.03 to about 0.4 grams per cubic centimeter.

23. The diaper according to claim 20 wherein the absorbent composite comprises the superabsorbent material in an amount of from about 5 to about 80 weight percent based on total weight of the absorbent composite.

24. The diaper according to claim 20 wherein, when said superabsorbent material is in the form of discrete particles, at least about 80%, by weight, of said superabsorbent material has a particle size greater than the median pore size of said porous fiber matrix.

25. A diaper, said diaper comprising:
a liquid-permeable facing material;
an absorbent composite adjacent said liquid-permeable facing material, said absorbent composite comprising a porous fiber matrix and an amount of a superabsorbent material present in said porous fiber matrix, wherein said porous fiber matrix comprises at least about 3%, by weight, based on porous fiber matrix weight of a fiber formed from a synthetic polymeric material, and further wherein said superabsorbent material can absorb at least about 24 milliliters of an aqueous solution of sodium chloride containing 0.9 weight percent, sodium chloride, per gram of superabsorbent material while under a restraining pressure of at least 21,000 dynes per square centimeter provided that, when said superabsorbent material is in the form of discrete particles, at least about 50%, by weight, of said superabsorbent material has a size greater than the median pore size of said porous fiber matrix when wet.

26. The diaper according to claim 25 wherein the porous fiber matrix comprises at least about 5%, by weight, of a fiber formed from a synthetic polymeric material.

27. The diaper according to claim 25 wherein the porous fiber matrix comprises wood pulp fluff.

28. The diaper according to claim 25 wherein the absorbent composite comprises the superabsorbent material in an amount of from about 5 to about 80 weight percent based on total weight of the absorbent composite.

29. The diaper according to claim 25 wherein, when said superabsorbent material is in the form of discrete particles, at least about 80%, by weight, of said superabsorbent material has a size greater than the median pore size of said porous fiber matrix.

30. The absorbent composite according to claim 1 wherein the superabsorbent material can absorb at least 29 milliliters of an aqueous solution of sodium chloride containing 0.9 weight percent sodium chloride per gram of superabsorbent material while under a restraining pressure of at least 21,000 dynes per square centimeter.

31. The absorbent composite according to claim 30 wherein said superabsorbent material can absorb at least 32 milliliters of an aqueous solution of sodium chloride containing 0.9 weight percent sodium chloride per gram of superabsorbent material while under a restraining pressure of at least 21,000 dynes per square centimeter.

32. The absorbent composite according to claim 14 wherein the superabsorbent material can absorb at least 27 milliliters of an aqueous solution of sodium chloride containing 0.9 weight percent sodium chloride per gram of superabsorbent material while under a restraining pressure of at least 21,000 dynes per square centimeter.

33. The absorbent composite according to claim 32 wherein the superabsorbent material can absorb at least 29 milliliters of an aqueous solution of sodium chloride containing 0.9 weight percent sodium chloride per gram of superabsorbent material while under a restraining pressure of at least 21,000 dynes per square centimeter.

34. The absorbent composite according to claim 14 wherein the superabsorbent material can absorb at least 32 milliliters of an aqueous solution of sodium chloride containing 0.9 weight percent sodium chloride per gram of superabsorbent material while under a restraining pressure of at least 21,000 dynes per square centimeter.

35. The diaper according to claim 20 wherein the superabsorbent material can absorb at least 29 milliliters of an aqueous solution of sodium chloride containing 0.9 weight percent sodium chloride per gram of superabsorbent material while under a restraining pressure of at least 21,000 dynes per square centimeter.

36. The diaper according to claim 35 wherein the superabsorbent material can absorb at least 32 milliliters of an aqueous solution of sodium chloride containing 0.9 weight percent sodium chloride per gram of superabsorbent material while under a restraining pressure of at least 21,000 dynes per square centimeter.

37. The diaper according to claim 25 wherein the superabsorbent material can absorb at least 27 milliliters of an aqueous solution of sodium chloride containing 0.9 weight percent sodium chloride per gram of superabsorbent material while under a restraining pressure of at least 21,000 dynes per square centimeter.

38. The diaper according to claim 37 wherein the superabsorbent material can absorb at least 29 milliliters of an aqueous solution of sodium chloride containing 0.9 weight percent sodium chloride per gram of superabsorbent material while under a restraining pressure of at least 21,000 dynes per square centimeter.

39. The diaper according to claim 38 wherein the superabsorbent material can absorb at least 32 milliliters of an aqueous solution of sodium chloride containing 0.9 weight percent sodium chloride per gram of superabsorbent material while under a restraining pressure of at least 21,000 dynes per square centimeter.

40. The absorbent composite according to claim 3, wherein the absorbent composite has a density of from about 0.08 to about 0.3 grams per cubic centimeter.

* * * * *

UNITED STATES PATENT AND TRADEMARK OFFICE
CERTIFICATE OF CORRECTION

PATENT NO. : 5,147,343
DATED : September 15, 1992
INVENTOR(S) : Stanley R. Kellenberger It is certified that error appears in the above-identified patent and that said Letters Patent is hereby corrected as shown below:

Column 19, Line 1, delete the number "22" and substitute therefor --21--.

Signed and Sealed this

Seventh Day of December, 1993

*Attest:*

BRUCE LEHMAN

*Attesting Officer*     *Commissioner of Patents and Trademarks*

REEXAMINATION CERTIFICATE (3466th)

United States Patent [19]

Kellenberger

[11] B1 5,147,343

[45] Certificate Issued Mar. 17, 1998

[54] ABSORBENT PRODUCTS CONTAINING HYDROGELS WITH ABILITY TO SWELL AGAINST PRESSURE

[75] Inventor: Stanley R. Kellenberger, Appleton, Wis.

[73] Assignee: Kimberly-Clark Corporation, Neenah, Wis.

Reexamination Request:
No. 90/004,270, Jun. 7, 1996

Reexamination Certificate for:
Patent No.: 5,147,343
Issued: Sep. 15, 1992
Appl. No.: 334,260
Filed: Apr. 10, 1989

Certificate of Correction issued Dec. 7, 1993.

Related U.S. Application Data

[63] Continuation-in-part of Ser. No. 184,302, Apr. 21, 1988, abandoned.

[51] Int. Cl.$^6$ .............................. A61F 13/15; A61F 13/20
[52] U.S. Cl. .................. 604/368; 604/372; 604/375; 428/281; 428/283

[56] References Cited

U.S. PATENT DOCUMENTS

| | | |
|---|---|---|
| Re. 32,649 | 4/1988 | Brandt et al. . |
| 2,810,716 | 10/1957 | Markus et al. . |
| 3,229,769 | 1/1966 | Bashaw et al. . |
| 3,589,364 | 6/1971 | Dean . |
| 3,669,103 | 6/1972 | Harper et al. . |
| 3,670,731 | 6/1972 | Harmon . |
| 3,901,236 | 8/1975 | Assarsson et al. . |
| 3,903,889 | 9/1975 | Torr . |
| 3,954,721 | 5/1976 | Gross . |
| 4,028,290 | 6/1977 | Reid . |
| 4,051,086 | 9/1977 | Reid . |
| 4,062,817 | 12/1977 | Westerman . |
| 4,069,177 | 1/1978 | Smith . |
| 4,076,663 | 2/1978 | Masuda et al. . |
| 4,090,013 | 5/1978 | Ganslaw et al. . |
| 4,102,340 | 7/1978 | Mesek et al. . |
| 4,104,214 | 8/1978 | Meierhoefer . |
| 4,105,033 | 8/1978 | Chatterjee et al. . |

(List continued on next page.)

FOREIGN PATENT DOCUMENTS

| | | |
|---|---|---|
| 1 104 002 | 6/1981 | Canada . |
| 0 122 042 | 10/1984 | European Pat. Off. . |
| 0 198 683 | 10/1986 | European Pat. Off. . |
| 0 202 125 | 11/1986 | European Pat. Off. . |
| 0 202 127 | 11/1986 | European Pat. Off. . |
| 0 205 674 | 12/1986 | European Pat. Off. . |
| 0 210 968 | 2/1987 | European Pat. Off. . |
| 0 212 618 | 3/1987 | European Pat. Off. . |
| 0 248 963 | 12/1987 | European Pat. Off. . |
| 0 254 476 | 1/1988 | European Pat. Off. . |
| 0 258 120 | 3/1988 | European Pat. Off. . |
| 77 510 | 4/1988 | European Pat. Off. . |
| 0 304 319 | 2/1989 | European Pat. Off. . |

(List continued on next page.)

OTHER PUBLICATIONS

M. Louis Arin, Ph.D., "Determination of the Fluid Capacity of Some Commercial Catamenial Tampons."

Dr. F. Masuda, Sanyo Chemical Industries Ltd., "The Concept of Superabsorbent Polymer," presented as paper No. 13 at the Pira Fibramerics Program held Dec. 1–3, 1987.

(List continued on next page.)

*Primary Examiner*—Paul Prebilic

[57] ABSTRACT

An absorbent composite of the type comprising a porous matrix of fibers and a supperabsorbent material dispersed among the interfiber spaces (pores) wherein the superabsorbent material exhibits the ability to absorb greater than about 24 milliliters of a saline solution per gram of superabsorbent material under an applied restraining force of at least about 21,000 dynes/square centimeter provided that, when in the form of discrete particles, at least about 50% of said superabsorbent material has a size greater than the median pore size of the matrix when wet.

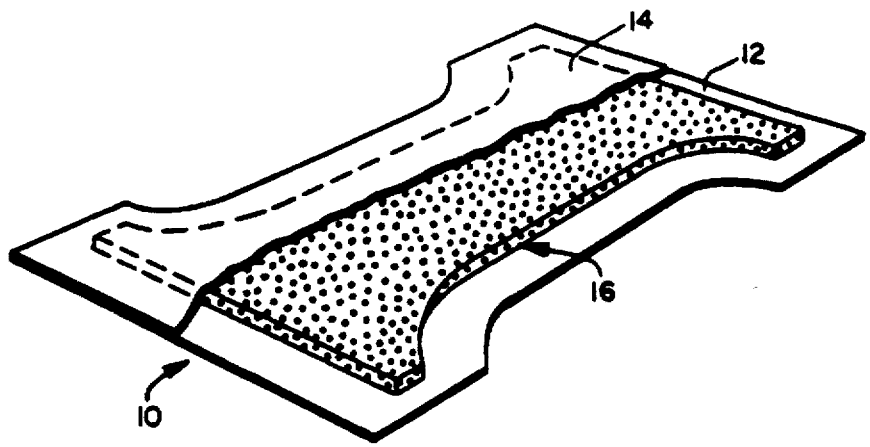

B1 5,147,343

U.S. PATENT DOCUMENTS

| | | |
|---|---|---|
| 4,128,692 | 12/1978 | Reid . |
| 4,155,893 | 5/1979 | Fujimoto et al. . |
| 4,200,557 | 4/1980 | Chatterjee et al. . |
| 4,242,408 | 12/1980 | Evani et al. . |
| 4,286,082 | 8/1981 | Tsubakimoto et al. . |
| 4,340,556 | 7/1982 | Ciencewicki . |
| 4,340,706 | 7/1982 | Obayashi et al. . |
| 4,357,827 | 11/1982 | McConnell . |
| 4,381,782 | 5/1983 | Mazurak et al. . |
| 4,389,487 | 6/1983 | Ries . |
| 4,473,689 | 9/1984 | Login et al. . |
| 4,535,098 | 8/1985 | Evani et al. . |
| 4,590,114 | 5/1986 | Holtman . |
| 4,604,313 | 8/1986 | McFarland et al. . |
| 4,610,678 | 9/1986 | Weisman et al. . |
| 4,640,810 | 2/1987 | Laursen et al. . |
| 4,650,127 | 3/1987 | Radwanski et al. . |
| 4,655,757 | 4/1987 | McFarland et al. . |
| 4,666,975 | 5/1987 | Yamasaki et al. . |
| 4,699,619 | 10/1987 | Bernardin . |
| 4,699,823 | 10/1987 | Kellenberger et al. . |
| 4,734,478 | 3/1988 | Tsubakimoto et al. . |
| 4,742,086 | 5/1988 | Masamizu et al. . |
| 4,755,562 | 7/1988 | Alexander et al. . |
| 4,773,903 | 9/1988 | Weisman et al. . |
| 4,798,603 | 1/1989 | Meyer et al. . |
| 4,820,773 | 4/1989 | Alexander et al. . |
| 4,834,735 | 5/1989 | Alemany et al. . |
| 4,954,652 | 9/1990 | Fritch et al. . |
| 5,061,259 | 10/1991 | Goldman et al. . |

FOREIGN PATENT DOCUMENTS

| | | |
|---|---|---|
| 0 317 106 | 5/1989 | European Pat. Off. . |
| 0 242 478 | 9/1990 | European Pat. Off. . |
| 2 293 914 | 9/1976 | France . |
| 2 222 780 | 11/1973 | Germany . |
| 35 23 617 | 1/1986 | Germany . |
| 3 313 344 | 4/1987 | Germany . |
| 56-140571 | 11/1981 | Japan . |
| 63-99861 | 5/1988 | Japan . |
| 63-275607 | 11/1988 | Japan . |
| 63-275608 | 11/1988 | Japan . |
| 719 330 | 12/1954 | United Kingdom . |
| 1 500 299 | 2/1978 | United Kingdom . |

OTHER PUBLICATIONS

Arakawa Technical Data by Arakawa Chemical (USA) Inc., 625 N. Michigan Ave., Suite 1700, Chicago, Ill. 60611, "Absorbency of Absorbent Polymer Under Pressure."

Aquareserve Technical Note, Nippon Gohsei, "High Water Absorbing Synthetic Resin," Technical Note No. 3.

P.K. Chatterjee, *Absorbency*, pp. 197–198, 1985.

B. Lichstein, "Demand Wettability, A New Method For Measuring Absorbency Characteristics Of Fabrics," INDA Technological Symposium Proceedings, Mar. 1974, pp. 129–142.

A. Burgeni et al., "Capillary Sorption Equilibria in Fiber Masses," *Textile Research Journal*, vol. 57, pp. 356–366 (May 1967).

"Standard Test Methods for Particle Size (Sieve Analysis) of Plastic Materials," American Society for Testing and Material Test Method D–1921, 1975.

R.E. Erickson, Dow Chemical U.S.A., "Absorbent Laminate For Low Bulk High Capacity Personal Care Products," Absorbent Products Conference Proceedings, Nov. 19, 1980.

P.J. George, B.F. Goodrich Chemical Group, "Surpon™—A New Superabsorbent Polymer For Absorbent Products," 1981 Proc. Absorbent Products Conference, Section III.

B. Lichstein, Ph. D., Johnson & Johnson Products, Inc., "The Demand Wettability Measurement of Absorbency Characteristics," Nov. 1980.

B. Lichstein, Ph.D., International Playtex, Inc., "Absorbent Characteristics, Mechanism and Measurement," TAPPI Int'l Dissolving Specialty Pulps Conference, Apr. 1983.

S. Martinis, et al., Weyerhauser Company, "Absorption of Liquids by Dry Fiber Networks," TAPPI Annual Meeting, Mar. 1981.

P. Maul, American Colloid Company, "Superabsorbents Breaking The Cellulose Cost Performance Barrier," presented at Insight Conference, Toronto Canada, Aug. 1986.

H. Mizutani, Kao Corporation, "Design Of Japanese Baby Diapers" presented at the Absorbent Products Conference, Sep. 23–24, 1987.

E.V. Painter, Johnson & Johnson, "Characterizing Absorbent Materials," 12th Annual INDA Technical Syimposium, May 22–23, 1984.

E.V. Painter, Johnson & Johnson, "Method for Evaluating Superabsorbent Specialty Polymers," presented at Proceedings of TAPPI Symposium on Nonwovens Conference, 1985.

R. Shishoo, Swedish Institute For Textile Research, "New Methods of Testing Absorbent Type Aids For Adult Incontinent Persons," 1981 Proc. Absorbent Products Conference, Section VI.

W. Tuerk et al., Stockhausen GmbH, "Testing Of Superabsorbents—Supposition For Their Appropriate Application In Disposables," Absorbent Products Conference, Oct. 13–14, 1982.

Chemdal Corporation, Procedure No. 8006, Feb. 1, 1986.

J. Hanson, Marketing/Technology Service, Inc., "Designing Better Superabsorbent Baby Diapers," *Nonwovens World*, May/Jun. 1987, pp. 69–74.

O.J. Kallmes et al, "The Gravimetric Absorbency Testing System," 1985 Nonwovens Symposium, pp. 231–235.

Test Sieves Table, Mechanical Engineering Pocketbook, vol. 1, 13th ed. rev., p. 903 (Berlin 1974).

H. Mizutani, Kao Corporation, "Designing Japanese Diapers Becoming A Growing Concern," *Nonwovens World*, Nov. 1987, pp. 39–42.

T. Dugdale, ARCO Chemical Company, "Novel Superabsorbent Fibers," *Nonwovens World*, Feb. 1987, pp. 107–110.

G.M. Aberson, "The Water Absorbency Of Pads Of Dry, Unbounded Fibers," pp. 282–307.

W. Dederichs, Starchem GmbH, "Superabsorbent Polymers: Their Properties Alone And In Combination With Fluff Particles," 2nd Int'l PIRA Nonwovens–Absorbency '89—Conference.

J. Hanson, Marketing/Technology Service, Inc., "How thin is thin?," Index 87 Congress, Session C2—Hygiene Solutions.

B. Miller et al., Textile Research Institute, "Pore Size Distribution From Measurements of Liquid Uptake and Retention," 11th Technical Symposium of Assoc. of the Nonwovens Fabrics Industry, Sep. 13–15, 1983.

P.G. Bither, Hercules, Inc., "Thermally Bonded Core—the Key to Value Added Absorbent Products," Nonwovens Business Conference, Insight '87, Sep. 20–22, 1987, Section X.

J. Hanson, Marketing/Technology Service, Inc., "Here Today, Gone Tomorrow—1987 Absorbent Markets Review," Insight '87 Conference, Sep. 23–24, 1987, Section X, pp. X–1 through X–31.

R. Schaff, "Impact of Recent Baby Diaper Design Changes On Machine Runnability and Efficiency," Insight '87 Conference, Sep. 23–24, 1987, Section XI, pp. XI–1 through XI–12.

J. Hanson, "Breathable Absorbent Disposables—Market Developments And The Future Market," *Nonwovens World*, Nov. 1986, pp. 102–108.

H. Dale Wilson, "Characterization of Pulpex E–338 Thermally Bonded Absorbent Cores," Insight '87 Conference, Sep. 23–24, 1987, Section IV.

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

ONLY THOSE PARAGRAPHS OF THE SPECIFICATION AFFECTED BY AMENDMENT ARE PRINTED HEREIN.

Column 2, lines 23–37:

Although the actual operating conditions used by current producers of SAP may vary, the patent literature teaches a broad range of temperature, concentrations, types of initiators and crosslinkers. Patents which disclose hydrogel-forming polymer compositions for use in absorbent structures are listed below:

U.S. Pat. No. 3,901,236 to Assarsson et al.
U.S. Pat. No. 4,062,817 to Westerman
U.S. Pat. No. 4,076,663 to Masuda et al.
U.S. Pat. No. 4,286,082 to Tsubakimoto et al.
U.S. Pat. No. 4,340,706 to Obayashi et al.
U.S. Pat. No. 4,473,689 to Login et al.
U.S. Pat. No. 4,535,098 to Evani et al.
European Patent [75,510] *77,510*
German Patent 3,313,344.

AS A RESULT OF REEXAMINATION, IT HAS BEEN DETERMINED THAT:

Claims 1, 14, 20, 25, 30, 31, 32 and 33–39 are determined to be patentable as amended.

Claims 2–13, 15–19, 21–24, 26–29 and 40, dependent on an amended claim, are determined to be patentable.

New claims 41–48 are added and determined to be patentable.

1. An absorbent composite comprising a porous fiber matrix and an amount of superabsorbent material present in said porous fiber matrix, wherein said superabsorbent material can absorb at least 27 milliliters of an aqueous solution of sodium chloride containing 0.9 weight percent, sodium chloride, per gram of superabsorbent material while under a restraining pressure of [at least] 21,000 dynes per square centimeter, provided that, when said superabsorbent material is in the form of discrete particles, at least about 50%, by weight, of said superabsorbent material has a size greater than the median pore size of said porous fiber matrix when wet.

14. An absorbent composite comprising a porous fiber matrix and an amount of superabsorbent material present in said porous fiber matrix, wherein said porous fiber matrix comprises at least about 3%, by weight, based on porous fiber matrix weight, of a synthetic polymeric fiber, and wherein said superabsorbent material can absorb at least about 24 milliliters of an aqueous solution of sodium chloride containing 0.9 weight percent, sodium chloride, per gram of superabsorbent material while under a restraining pressure of [at least] 21,000 dynes per square centimeter provided that, when said superabsorbent material is in the form of discrete particles, at least about 50%, by weight, of said superabsorbent material has a size greater than the median pore size of said porous fiber matrix when wet.

20. A diaper, said diaper comprising:
a liquid-permeable facing material;
an absorbent composite adjacent said liquid-permeable facing material, said absorbent composite comprising a porous fiber matrix and an amount of a superabsorbent material present in said porous fiber matrix, wherein said superabsorbent material can absorb at least 27 milliliters of an aqueous solution of sodium chloride containing 0.9 weight percent sodium chloride, per gram of superabsorbent material while under a restraining pressure of [at least] 21,000 dynes per square centimeter, provided that, when said superabsorbent material is in the form of discrete particles, at least about 50%, by weight, of said superabsorbent material has a particle size greater than the median pore size of said porous fiber matrix when wet; and
a liquid-impermeable backing material adjacent said absorbent composite and located opposite said liquid-permeable facing material.

25. A diaper, said diaper comprising:
a liquid-permeable facing material;
an absorbent composite adjacent said liquid-permeable facing material, said absorbent composite comprising a porous fiber matrix and an amount of a superabsorbent material present in said porous fiber matrix, wherein said porous fiber matrix comprises at least about 3%, by weight, based on porous fiber matrix weight, of a fiber formed from a synthetic polymeric material, and further wherein said superabsorbent material can absorb at least about 24 milliliters of an aqueous solution of sodium chloride containing 0.9 weight percent, sodium chloride, per gram of superabsorbent material while under a restraining pressure of [at least] 21,000 dynes per square centimeter provided that, when said superabsorbent material is in the form of discrete particles, at least about 50%, by weight, of said superabsorbent material has a size greater than the median pore size of said porous fiber matrix when wet.

30. The absorbent composite according to claim 1 wherein the superabsorbent material can absorb at least 29 milliliters of an aqueous solution of sodium chloride containing 0.9 weight percent sodium chloride per gram of superabsorbent material while under a restraining pressure of [at least] 21,000 dynes per square centimeter.

31. The absorbent composite according to claim 30 wherein said superabsorbent material can absorb at least 32 milliliters of an aqueous solution of sodium chloride containing 0.9 weight percent sodium chloride per gram of superabsorbent material while under a restraining pressure of [at least] 21,000 dynes per square centimeter.

32. The absorbent composite according to claim 14 wherein the superabsorbent material can absorb at least 27 milliliters of an aqueous solution of sodium chloride containing 0.9 weight percent sodium chloride per gram of superabsorbent material while under a restraining pressure of [at least] 21,000 dynes per square centimeter.

33. The absorbent composite according to claim 32 wherein the superabsorbent material can absorb at least 29 milliliters of an aqueous solution of sodium chloride containing 0.9 weight percent sodium chloride per gram of superabsorbent material while under a restraining pressure of [at least] 21,000 dynes per square centimeter.

34. The absorbent composite according to claim 14 wherein the superabsorbent material can absorb at least 32 milliliters of an aqueous solution of sodium chloride containing 0.9 weight percent sodium chloride per gram of superabsorbent material while under a restraining pressure of [at least] 21,000 dynes per square centimeter.

35. The diaper according to claim 20 wherein the superabsorbent material can absorb at least 29 milliliters of an aqueous solution of sodium chloride containing 0.9 weight percent sodium chloride per gram of superabsorbent material while under a restraining pressure of [at least] 21,000 dynes per square centimeter.

36. The diaper according to claim 35 wherein the superabsorbent material can absorb at least 32 milliliters of an aqueous solutions of sodium chloride containing 0.9 weight percent sodium chloride per gram of superabsorbent material while under a restraining pressure of [at least] 21,000 per square centimeter.

37. The diaper according to claim 25 wherein the superabsorbent material can absorb at least 27 milliliters of an aqueous solution of sodium chloride containing 0.9 weight percent sodium chloride per gram of superabsorbent material while under a restraining pressure of [at least] 21,000 dynes per square centimeter.

38. The diaper according to claim 37 wherein the superabsorbent material can absorb at least 29 milliliters of an aqueous solution of sodium chloride containing 0.9 weight percent sodium chloride per gram of superabsorbent material while under a restraining pressure of [at least] 21,000 dynes per square centimeter.

39. The diaper according to claim 38 wherein the superabsorbent material can absorb at least 32 milliliters of an aqueous solution of sodium chloride containing 0.9 weight percent sodium chloride per gram of superabsorbent material while under a restraining pressure of [at least] 21,000 dynes per square centimeter.

41. An absorbent composite comprising a porous fiber matrix and an amount of superabsorbent material present in the form of discrete particles dispersed among interfiber pores in said porous fiber matrix; wherein said superabsorbent material can absorb at least 27 milliliters of an aqueous solution of sodium chloride containing 0.9 weight percent sodium chloride, per gram of superabsorbent material while under a restraining pressure of 21,000 dynes per square centimeter; and further wherein at least about 50% by weight of said superabsorbent material has a size greater than the median pore size of said porous fiber matrix when wet.

42. The absorbent composite according to claim 41, wherein the superabsorbent material can absorb at least 29 milliliters of an aqueous solution of sodium chloride containing 0.9 weight percent sodium chloride per gram of superabsorbent material while under a restraining pressure of 21,000 dynes per square centimeter.

43. The absorbent composite according to claim 42, wherein the superabsorbent material can absorb at least 32 milliliters of an aqueous solution of sodium chloride containing 0.9 weight percent sodium chloride per gram of superabsorbent material while under a restraining pressure of 21,000 dynes per square centimeter.

44. A diaper comprising the absorbent composite of claim 41 incorporated therein, said diaper further comprising:

a liquid permeable facing material adjacent to said absorbent composite; and a liquid impermeable backing material adjacent to said absorbent composite and located opposite said liquid permeable facing material.

45. The diaper according to claim 44, wherein at least about 80% by weight of said superabsorbent material has a particle size greater than the median pore size of said porous fiber matrix, when wet.

46. An absorbent composite comprising a porous fibrous matrix and an amount of superabsorbent material present in said porous fibrous matrix in the form of discrete particles dispersed in pores between fibers of the matrix;

wherein the superabsorbent material can absorb at least 27 milliliters of an aqueous solution of sodium chloride containing 0.9 weight percent sodium chloride, per gram of superabsorbent material while under a restraining pressure of 21000 dynes per square centimeter;

and wherein at least about 50% by weight of said superabsorbent material has a particle size in an unswollen condition which is greater than the median pore size of the porous fiber matrix when wet, and wherein said superabsorbent material contains sufficient amounts of said particles sized so as to swell during absorption to push fibers apart and maintain open capillary structures in the matrix.

47. The absorbent composite of claim 46, wherein said at least about 50% by weight of said superabsorbent material in said unswollen condition comprises particles having sizes greater than about 100 microns.

48. A diaper comprising the absorbent composite of claim 46 incorporated therein, said diaper further comprising:

a liquid permeable facing material adjacent to said absorbent composite; and a liquid impermeable backing material adjacent to said absorbent composite and located opposite said liquid permeable facing material.

* * * * *